United States Patent [19]
Oppenheim et al.

[11] Patent Number: 5,885,965
[45] Date of Patent: Mar. 23, 1999

[54] ANTI-FUNGAL D-AMINO ACID HISTATIN-BASED PEPTIDES

[75] Inventors: Frank G. Oppenheim, Chestnut Hill; Tao Xu, Newton; F. Donald Roberts, Dover; Peter Spacciapoli, Newbury; Phillip M. Friden, Bedford, all of Mass.

[73] Assignees: Periodontix, Inc., Watertown, Mass.; Trustees of Boston University, Boston, Mass.

[21] Appl. No.: 973,563

[22] PCT Filed: Jun. 7, 1996

[86] PCT No.: PCT/US96/09962

§ 371 Date: Mar. 12, 1998

§ 102(e) Date: Mar. 12, 1998

[87] PCT Pub. No.: WO96/40770

PCT Pub. Date: Dec. 19, 1996

Related U.S. Application Data

[63] Continuation-in-part of Ser. No. 485,273, Jun. 7, 1995, Pat. No. 5,631,228, which is a continuation-in-part of Ser. No. 287,717, Aug. 9, 1994, Pat. No. 5,486,503, which is a continuation of Ser. No. 145,030, Oct. 28, 1993, abandoned, which is a continuation of Ser. No. 786,571, Nov. 1, 1991, abandoned.

[51] Int. Cl.⁶ .......................... A61K 38/08; A61K 38/10; C07K 7/06; C07K 7/08
[52] U.S. Cl. ................................ 514/12; 514/13; 514/14; 514/15; 530/324; 530/325; 530/326; 530/327
[58] Field of Search .................... 514/2, 12, 13, 514/14, 15, 16; 530/324, 325, 326, 327

[56] References Cited

U.S. PATENT DOCUMENTS

| | | | |
|---|---|---|---|
| 4,725,576 | 2/1988 | Pollock et al. | 514/2 |
| 4,734,400 | 3/1988 | Bolin et al. | 514/12 |
| 4,962,277 | 10/1990 | Cuervo et al. | 514/14 |
| 5,032,574 | 7/1991 | Wilde et al. | 514/12 |
| 5,190,920 | 3/1993 | Eyal et al. | 514/17 |
| 5,221,732 | 6/1993 | Chen et al. | 530/326 |
| 5,225,399 | 7/1993 | Zasloff et al. | 514/13 |
| 5,239,059 | 8/1993 | Zasloff et al. | 530/325 |
| 5,304,633 | 4/1994 | Tomita et al. | 530/327 |
| 5,324,716 | 6/1994 | Selsted et al. | 514/14 |
| 5,409,898 | 4/1995 | Darveau et al. | 514/13 |
| 5,424,290 | 6/1995 | Maloy et al. | 514/13 |
| 5,447,914 | 9/1995 | Travis et al. | 514/16 |
| 5,459,237 | 10/1995 | Berkowitz et al. | 530/326 |
| 5,464,823 | 11/1995 | Lehrer et al. | 514/13 |
| 5,470,950 | 11/1995 | Maloy et al. | 530/324 |
| 5,486,503 | 1/1996 | Oppenheim et al. | 514/2 |
| 5,504,190 | 4/1996 | Houghton et al. | 530/329 |
| 5,519,115 | 5/1996 | Mapelli et al. | 530/324 |
| 5,547,939 | 8/1996 | Selsted | 514/14 |
| 5,549,894 | 8/1996 | Hunt | 424/94.64 |
| 5,631,823 | 5/1997 | Oppenheim et al. | 514/13 |
| 5,646,119 | 7/1997 | Oppenheim et al. | 514/12 |
| 5,652,332 | 7/1997 | Little, II | 530/324 |
| 5,688,767 | 11/1997 | Hancock et al. | 514/12 |
| 5,693,486 | 12/1997 | Lehrer et al. | 435/69.1 |
| 5,708,145 | 1/1998 | Lehrer et al. | 530/387.1 |

FOREIGN PATENT DOCUMENTS

| | | |
|---|---|---|
| 3-261747 | 8/1994 | Japan. |
| 6-234653 | 8/1994 | Japan. |
| 6-287146 | 10/1994 | Japan. |
| WO 94/21672 | 9/1994 | WIPO. |

OTHER PUBLICATIONS

Sugiyama, K., et al., Japanese Journal of Oral Biology, vol. 27, "The amino acid sequence of a salivary peptide (F–A) with histamine–releasing properties", pp. 1252–1253, 1985.

(List continued on next page.)

Primary Examiner—Robert A. Wax
Assistant Examiner—William W. Moore
Attorney, Agent, or Firm—Hamilton, Brook, Smith & Reynolds, P.C.

[57] ABSTRACT

D-amino acid histatins and histatin-based peptides and methods for treatment of fungal or bacterial infection are described. These D-amino acid histatins and histatin-based peptides are longer-acting anti-fungal or anti-bacterial agents than their L-enantiomeric analogues.

22 Claims, 12 Drawing Sheets

OTHER PUBLICATIONS

Sabatini, L. M., et al., Biochemical and Biophysical Research Communications, vol. 160, "Histatins, a family of salivary histidine–rich proteins are encoded by at least two loci (HIS1 and HIS2)", pp. 495–502, 1989.

Sugiyama, K., et al., Archives of Oral Biology, vol. 35, "Rapid purification and characterization of histatins (histidine–rich polypeptides) from human whole slaiva", pp. 415–419, 1990.

VanderSpek, J. C., et al., Archives of Oral Biology, vol. 35, "Molecular cloning of human submandibular histatins", pp. 137–143, 1990.

Wade, R., et al., Proceedings of the National Academy of Sciences, U.S.A., vol. 87, "All –D–amino acid–containing channels forming antibiotic peptides", pp. 476–4765, 1990.

Bessalle, R., et al., FEBS Letters, vol. 274, "All–D–magainin: Chirality, antimicrobial activity and proteolytic resistance", pp. 151–155, 1990.

Chang, C. C., et al., in PEPTIDES 1990, Giralt, E., et al., Eds., "Synthesis and biological activity of histidine–rich peptides bonded to polylysine backbone", pp. 843–846, ESCOM, Pub. Leiden, 1991.

Lai, k., et al., Archives of Oral Biology, vol. 37, "The use of capillary electrophoresis to identify cationid proteins in human parotid saliva", pp. 7–13, 1992.

Sabatini, L. M., et al., Molecular Biology and Evolution, vol. 10, "Nucleotide sequence anlaysis of the human salivary proteins genes HLS1 and HLS2 and evolution of the STATH/HIS gene family", pp. 497–511, 1993.

Richardson, C. F., et al., Archives of Oral Biology, vol. 38, "The influence of histatin–5 fragments on the mineralization of hydroxyapatite," pp. 997–1002, 1993.

Driscoll, J., et al., Gene, vol. 177, "Candidacidal activity of human salivary histatin recombinant variants produced by site–directed mutagenesis", pp. 29–34, 1996.

Tsai, H., et al., Infection and Immunity, vol. 64, "Candidacidal activity of recombinant human salivary histatin–5 and variants", pp. 50000–5007, 1996.

Murakami, Y. et al., "Inhibitory Effects of Synthetic Histidine–Rich Peptides on Haemagglutination by Bacteroides Gingivalis 381", Arch. Oral Biol., 35(9): 775–777 (1990).

Oppenheim, F.G. et al., "Histatins, a Novel Family of Histidine–Rich Proteins in Human Paretoid Secretion", J. Biol. Chem., 263 (16) :7472–7477 (Jun. 1988).

Xu, T. et al., "Anticandial Activity of Major Human Salivary Histatins", Infect. Immunol., 59 (8) :2549–2554 (Aug. 1991).

Xu, T. et al., "Anti–fungal Functional Domain of Histatin 3", J. Dent. Res. 70:497 (Apr. 1991).

Raj, P.A. et al., "Salivary Histatin 5: Depnedence of Sequence, Chain Length, and Helical Confirmation for Candidacidal Activity", J. Biol. Chem.,265 (7) :3898 (Mar. 15, 1990).

Santarpia III, R.P. et al., "A Comparison of the Inhibition of Blastospore Viability and Germ–Tube Development in Candida Albicans by Histidine Peptides and Ketoconazole", Arch. Oral Biol., 33 (8) :567–573 (1988).

Santarpia III, R.P. et al., "Preliminary Findings for In Vivo Efficacy of Salivary Histidine–Rich Polypeptides", J. Dent. Res., 69:173 (Mar. 1990).

Troxler, R.F. et al., "Structural Relationship Between Human Salivary Histatins", J. Dent. Res., 69(1) :2–6 (Jan. 1990).

Xu, T. et al., "Primary Structure and Anticandidal Activity of the Major Histatin from Parotid Secretion of the Subhuman Primate, Macac fascicularis," J. Dent. Res., 69(11) :1717–1723 (Nov. 1990).

Xu, T. et al., "Structure/Function Analysis of Anti–Candida Activities of Histatin 1," J. Dent. Res., 68:973 (Jun. 1989).

Nishikata, M. et al., "Salivary Histatin as an Inhibitor of a Protease Produced by the Oral Bacterium Bacteroides gingivalis," Biochem. Biophys. Res. Comm., 174(2):625–630 (Jan 31, 1991).

Zuo, Y., et Al., Gene, vol. 161, "Recombinant histatins: functional domain duplication enhances candidacidal activity", pp. 87–91, 1995.

Edgerton, M. et al. Journal of Biomedical Materials Research, vol. 29, "Surface–modified poly(methyl methylacrylate) enhances adsorption and retains anticandidal activities of salivary histatin 5", pp. 1277–289, 1995.

Histatin 1:  Asp-Pse-His-Glu-Lys-Arg-His-His-Gly-Tyr-Arg-Arg-Lys-Phe-His-Glu-Lys-His-His- Histatin 2:  Arg-Lys-Phe-His-Glu-Lys-His-His- Histatin 3:  Asp-Ser-His-Ala-Lys-Arg-His-His-Gly-Tyr-Lys-Arg-Lys-Phe-His-Glu-Lys-His-His- Histatin 4:  Arg-Lys-Phe-His-Glu-Lys-His-His- Histatin 5:  Asp-Ser-His-Ala-Lys-Arg-His-His-Gly-Tyr-Lys-Arg-Lys-Phe-His-Glu-Lys-His-His- Histatin 6:  Asp-Ser-His-Ala-Lys-Arg-His-His-Gly-Tyr-Lys-Arg-Lys-Phe-His-Glu-Lys-His-His- Histatin 7:  Arg-Lys-Phe-His-Glu-Lys-His-His- Histatin 8:  Lys-Phe-His-Glu-Lys-His-His- Histatin 9:  Arg-Lys-Phe-His-Glu-Lys-His-His- Histatin 10: Lys-Phe-His-Glu-Lys-His-His- Histatin 11: Lys-Arg-His-His-Gly-Tyr-Lys-Arg Histatin 12: Lys-Arg-His-His-Gly-Tyr-Lys Peptide 101: Lys-Arg-His-His-Gly-Tyr-Lys-Arg-Lys-Phe-His-Glu-Lys-His-His- Peptide 102: Gly-Tyr-Lys-Arg-Lys-Phe-His-Glu-Lys-His-His- Peptide 103: Lys-Arg-His-His-Gly-Tyr-Lys-Arg-Lys-Phe-His-Glu-Lys-His-His-

FIGURE 1A

```
Peptide 104:                   Gly-Tyr-Lys-Arg-Lys-Phe-His-Glu-Lys-His-His-
Peptide 105:     Lys-Arg-His-His-Gly-Tyr-Lys-Arg-Lys-Phe-His-Glu-Lys-His-His
Peptide 113:     Ala-Lys-Arg-His-His-Gly-Tyr-Lys-Arg-Lys-Phe-His
Peptide 113-F4:  Ala-Lys-Arg-Phe-His-Gly-Tyr-Lys-Arg-Lys-Phe-His
Peptide 113-F5:  Ala-Lys-Arg-His-Phe-Gly-Tyr-Lys-Arg-Lys-Phe-His
Peptide 113-F12: Ala-Lys-Arg-His-His-Gly-Tyr-Lys-Arg-Lys-Phe-Phe
Peptide 113-F4.5: Ala-Lys-Arg-Phe-Phe-Gly-Tyr-Lys-Arg-Lys-Phe-Phe
Peptide 113-F4.5.12: Ala-Lys-Arg-Phe-Phe-Gly-Tyr-Lys-Arg-Lys-Phe-Phe
Peptide 113-K6:  Ala-Lys-Arg-His-His-Lys-Tyr-Lys-Arg-Lys-Phe-His
Peptide 113-H8:  Ala-Lys-Arg-His-His-Gly-Tyr-His-Arg-Lys-Phe-His
Peptide 113-K6H8: Ala-Lys-Arg-His-His-Lys-Tyr-His-Arg-Lys-Phe-His
Peptide 113-F8:  Ala-Lys-Arg-His-His-Gly-Tyr-Phe-Arg-Lys-Phe-His
Peptide 113-L4.5.12: Ala-Lys-Arg-Leu-Leu-Gly-Tyr-Lys-Arg-Lys-Phe-Leu
Peptide 113-Y4.5.12: Ala-Lys-Arg-Tyr-Tyr-Gly-Tyr-Lys-Arg-Lys-Phe-Tyr
Peptide 113-Q2.10: Ala-Gln-Arg-His-His-Gly-Tyr-Lys-Arg-Gln-Phe-His
```

FIGURE 1B

```
Peptide 113-Q3.9:      Ala-Lys-Gln-His-His-Gly-Tyr-Lys-Gln-Lys-Phe-His
Peptide 113-Q2.3.9.10: Ala-Gln-Gln-His-His-Gly-Tyr-Lys-Gln-Lys-Phe-His
Peptide 117:                   Lys-Arg-His-His-Gly-Tyr-Lys-Arg-Lys-Phe-His
Peptide 118:           Ala-Lys-Arg-His-His-Gly-Tyr-Lys-Arg-Lys-Phe
Peptide 119:           Ala-Lys-Arg-His-His-Gly-Tyr-Lys-Arg-Lys
Peptide 120:           Ala-Lys-Arg-His-His-Gly-Tyr-Lys-Arg
Peptide 129:                   Lys-Arg-His-His-Gly-Tyr-Lys-Arg-Lys-Phe Histatin 1: Ser-His-Arg-Glu-Phe-Pro-Phe-Tyr-Gly-Asp-Tyr-Gly-Ser-Asn-Tyr-Leu-Tyr-Asp-Asn
Histatin 2: Ser-His-Arg-Glu-Phe-Pro-Phe-Tyr-Gly-Asp-Tyr-Gly-Ser-Asn-Tyr-Leu-Tyr-Asp-Asn
Histatin 3: Ser-His-Arg-Gly-Tyr-Arg-Ser-Asn-Tyr-Leu-Tyr-Asp-Asn
Histatin 4: Ser-His-Arg-Gly-Tyr-Arg-Ser-Asn-Tyr-Leu-Tyr-Asp-Asn
Histatin 5: Ser-His-Arg-Gly-Tyr
Histatin 6: Ser-His-Arg-Gly-Tyr-Arg
Histatin 7: Ser-His-Arg-Gly-Tyr
Histatin 8: Ser-His-Arg-Gly-Tyr
```

FIGURE 1C

```
                      20                    25
Histatin 9:   Ser-His-Arg-Gly-Tyr-Arg Histatin 10:  Ser-His-Arg-Gly-Tyr-Arg Peptide 101:  Ser-His-Arg-Gly-Tyr-Arg Peptide 102:  Ser-His-Arg-Gly-Tyr-Arg Peptide 103:  Ser-His-Arg Peptide 104:  Ser-His-Arg
```

FIGURE 1D

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
( A ) LENGTH: 38 amino acids
( B ) TYPE: amino acid
( C ) STRANDEDNESS:
( D ) TOPOLOGY: linear ( i i ) MOLECULE TYPE: peptide ( i x ) FEATURE:
( A ) NAME/KEY: Modified-site
( B ) LOCATION: 2
( D ) OTHER INFORMATION: /product="PSE"

( i x ) FEATURE:
( A ) NAME/KEY: Region
( B ) LOCATION: 1..38
( D ) OTHER INFORMATION: /note= "At least one amino acid must have a D configuration."

( x i ) SEQUENCE DESCRIPTION: SEQ ID NO:1:

```
Asp  Xaa  His  Glu  Lys  Arg  His  His  Gly  Tyr  Arg  Arg  Lys  Phe  His  Glu
1                   5                        10                       15
Lys  His  His  Ser  His  Arg  Glu  Phe  Pro  Phe  Tyr  Gly  Asp  Tyr  Gly  Ser
               20                      25                       30
Asn  Tyr  Leu  Tyr  Asp  Asn
               35
```

( 2 ) INFORMATION FOR SEQ ID NO:2:

( i ) SEQUENCE CHARACTERISTICS:
( A ) LENGTH: 27 amino acids
( B ) TYPE: amino acid
( C ) STRANDEDNESS:
( D ) TOPOLOGY: linear ( i i ) MOLECULE TYPE: peptide ( i x ) FEATURE:
( A ) NAME/KEY: Region
( B ) LOCATION: 1..27
( D ) OTHER INFORMATION: /note= "At least one amino acid must have a D configuration"

( x i ) SEQUENCE DESCRIPTION: SEQ ID NO:2:

```
Arg  Lys  Phe  His  Glu  Lys  His  His  Ser  His  Arg  Glu  Phe  Pro  Phe  Tyr
1                   5                        10                       15
Gly  Asp  Tyr  Gly  Ser  Asn  Tyr  Leu  Tyr  Asp  Asn
               20                      25
```

( 2 ) INFORMATION FOR SEQ ID NO:3:

( i ) SEQUENCE CHARACTERISTICS:
        ( A ) LENGTH: 32 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Region
        ( B ) LOCATION: 1..32
        ( D ) OTHER INFORMATION: /note= "At least one amino acid
              must have a D configuration."

( x i ) SEQUENCE DESCRIPTION: SEQ ID NO:3:

```
Asp  Ser  His  Ala  Lys  Arg  His  His  Gly  Tyr  Lys  Arg  Lys  Phe  His  Glu
1                   5                        10                       15
Lys  His  His  Ser  His  Arg  Gly  Tyr  Arg  Ser  Asn  Tyr  Leu  Tyr  Asp  Asn
                    20                       25                       30
```

( 2 ) INFORMATION FOR SEQ ID NO:4:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Region
        ( B ) LOCATION: 1..21
        ( D ) OTHER INFORMATION: /note= "At least one amino acid
              must have a D configuration."

( x i ) SEQUENCE DESCRIPTION: SEQ ID NO:4:

```
Arg  Lys  Phe  His  Glu  Lys  His  His  Ser  His  Arg  Gly  Tyr  Arg  Ser  Asn
1                   5                        10                       15
Tyr  Leu  Tyr  Asp  Asn
                    20
```

( 2 ) INFORMATION FOR SEQ ID NO:5:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Region
        ( B ) LOCATION: 1..24
        ( D ) OTHER INFORMATION: /note= "At least one amino acid
              must have a D configuration."

( x i ) SEQUENCE DESCRIPTION: SEQ ID NO:5:

```
Asp  Ser  His  Ala  Lys  Arg  His  His  Gly  Tyr  Lys  Arg  Lys  Phe  His  Glu
1                   5                        10                       15
Lys  His  His  Ser  His  Arg  Gly  Tyr
                    20
```

( 2 ) INFORMATION FOR SEQ ID NO:6:

( i ) SEQUENCE CHARACTERISTICS:
        ( A ) LENGTH: 25 amino acids (B) TYPE: amino acid
(C) STRANDEDNESS:
(D) TOPOLOGY: linear (ii) MOLECULE TYPE: peptide (ix) FEATURE:
(A) NAME/KEY: Region
(B) LOCATION: 1..25
(D) OTHER INFORMATION: /note= "At least one amino acid must have a D configuration."

(xi) SEQUENCE DESCRIPTION: SEQ ID NO:6:

```
Asp  Ser  His  Ala  Lys  Arg  His  His  Gly  Tyr  Lys  Arg  Lys  Phe  His  Glu
1              5                        10                            15
Lys  His  His  Ser  His  Arg  Gly  Tyr  Arg
             20                       25
```

(2) INFORMATION FOR SEQ ID NO:7:

(i) SEQUENCE CHARACTERISTICS:
(A) LENGTH: 13 amino acids
(B) TYPE: amino acid
(C) STRANDEDNESS:
(D) TOPOLOGY: linear (ii) MOLECULE TYPE: peptide (ix) FEATURE:
(A) NAME/KEY: Region
(B) LOCATION: 1..13
(D) OTHER INFORMATION: /note= "At least one amino acid must have a D configuration."

(xi) SEQUENCE DESCRIPTION: SEQ ID NO:7:

```
Arg  Lys  Phe  His  Glu  Lys  His  His  Ser  His  Arg  Gly  Tyr
1              5                        10
```

(2) INFORMATION FOR SEQ ID NO:8:

(i) SEQUENCE CHARACTERISTICS:
(A) LENGTH: 12 amino acids
(B) TYPE: amino acid
(C) STRANDEDNESS:
(D) TOPOLOGY: linear (ii) MOLECULE TYPE: peptide (ix) FEATURE:
(A) NAME/KEY: Region
(B) LOCATION: 1..12
(D) OTHER INFORMATION: /note= "At least one amino acid must have a D configuration."

(xi) SEQUENCE DESCRIPTION: SEQ ID NO:8:

```
Lys  Phe  His  Glu  Lys  His  His  Ser  His  Arg  Gly  Tyr
1              5                        10
```

(2) INFORMATION FOR SEQ ID NO:9:

(i) SEQUENCE CHARACTERISTICS:
(A) LENGTH: 14 amino acids
(B) TYPE: amino acid
(C) STRANDEDNESS:
(D) TOPOLOGY: linear (ii) MOLECULE TYPE: peptide (ix) FEATURE:
(A) NAME/KEY: Region
(B) LOCATION: 1..14
(D) OTHER INFORMATION: /note= "At least one amino acid must have a D configuration."

( x i ) SEQUENCE DESCRIPTION: SEQ ID NO:9:

Arg Lys Phe His Glu Lys His His Ser His Arg Gly Tyr Arg
1               5                       10

( 2 ) INFORMATION FOR SEQ ID NO:10:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Region
        ( B ) LOCATION: 1..13
        ( D ) OTHER INFORMATION: /note= "At least one amino acid
            must have a D configuration."

( x i ) SEQUENCE DESCRIPTION: SEQ ID NO:10:

Lys Phe His Glu Lys His His Ser His Arg Gly Tyr Arg
1               5                   10

( 2 ) INFORMATION FOR SEQ ID NO:11:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Region
        ( B ) LOCATION: 1..8
        ( D ) OTHER INFORMATION: /note= "At least one amino acid
            must have a D configuration."

( x i ) SEQUENCE DESCRIPTION: SEQ ID NO:11:

Lys Arg His His Gly Tyr Lys Arg
1               5

( 2 ) INFORMATION FOR SEQ ID NO:12:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Region
        ( B ) LOCATION: 1..7
        ( D ) OTHER INFORMATION: /note= "At least one amino acid
            must have a D configuration."

( x i ) SEQUENCE DESCRIPTION: SEQ ID NO:12:

Lys Arg His His Gly Tyr Lys
1               5

( 2 ) INFORMATION FOR SEQ ID NO:13:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
    ( A ) NAME/KEY: Region
    ( B ) LOCATION: 1..21
    ( D ) OTHER INFORMATION: /note= "At least one amino must
        have a D configuration."

( x i ) SEQUENCE DESCRIPTION: SEQ ID NO:13:

```
Lys Arg His His Gly Tyr Lys Arg Lys Phe His Glu Lys His His Ser
1               5                   10                  15

His Arg Gly Tyr Arg
            20
```

( 2 ) INFORMATION FOR SEQ ID NO:14:

( i ) SEQUENCE CHARACTERISTICS:
        ( A ) LENGTH: 17 amino acids
        ( B ) TYPE: amino acid
        ( C ) STRANDEDNESS:
        ( D ) TOPOLOGY: linear ( i i ) MOLECULE TYPE: peptide ( i x ) FEATURE:
    ( A ) NAME/KEY: Region
    ( B ) LOCATION: 1..17
    ( D ) OTHER INFORMATION: /note= "At least one amino acid
        must have a D configuration."

( x i ) SEQUENCE DESCRIPTION: SEQ ID NO:14:

```
Gly Tyr Lys Arg Lys Phe His Glu Lys His His Ser His Arg Gly Tyr
1               5                   10                  15

Arg
```

( 2 ) INFORMATION FOR SEQ ID NO:15:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( i x ) FEATURE:
    ( A ) NAME/KEY: Region
    ( B ) LOCATION: 1..18
    ( D ) OTHER INFORMATION: /note= "At least one amino acid
        must have a D configuration."

( x i ) SEQUENCE DESCRIPTION: SEQ ID NO:15:

```
Lys Arg His His Gly Tyr Lys Arg Lys Phe His Glu Lys His His Ser
1               5                   10                  15

His Arg
```

( 2 ) INFORMATION FOR SEQ ID NO:16:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: linear ( i i ) MOLECULE TYPE: peptide ( i x ) FEATURE:
    ( A ) NAME/KEY: Region
    ( B ) LOCATION: 1..14
    ( D ) OTHER INFORMATION: /note= "At least one amino acid must have a D configuration."

( x i ) SEQUENCE DESCRIPTION: SEQ ID NO:16:

```
Gly  Tyr  Lys  Arg  Lys  Phe  His  Glu  Lys  His  His  Ser  His  Arg
1                   5                        10
```

( 2 ) INFORMATION FOR SEQ ID NO:17:

( i ) SEQUENCE CHARACTERISTICS:
        ( A ) LENGTH: 15 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Region
        ( B ) LOCATION: 1..15
        ( D ) OTHER INFORMATION: /note= "At least one amino acid
            must have a D configuration."

( x i ) SEQUENCE DESCRIPTION: SEQ ID NO:17:

```
Lys  Arg  His  His  Gly  Tyr  Lys  Arg  Lys  Phe  His  Glu  Lys  His  His
1                   5                        10                       15
```

( 2 ) INFORMATION FOR SEQ ID NO:18:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Region
        ( B ) LOCATION: 1..12
        ( D ) OTHER INFORMATION: /note= "At least one amino acid
            must have a D configuration."

( x i ) SEQUENCE DESCRIPTION: SEQ ID NO:18:

```
Ala  Lys  Arg  His  His  Gly  Tyr  Lys  Arg  Lys  Phe  His
1                   5                        10
```

( 2 ) INFORMATION FOR SEQ ID NO:19:

( i ) SEQUENCE CHARACTERISTICS:
        ( A ) LENGTH: 11 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Region
        ( B ) LOCATION: 1..11
        ( D ) OTHER INFORMATION: /note= "At least one amino acid
            must have a D configuration."

( x i ) SEQUENCE DESCRIPTION: SEQ ID NO:19:

```
Lys  Arg  His  His  Gly  Tyr  Lys  Arg  Lys  Phe  His
1                   5                        10
```

( 2 ) INFORMATION FOR SEQ ID NO:20:

( i ) SEQUENCE CHARACTERISTICS:
        ( A ) LENGTH: 11 amino acids
        ( B ) TYPE: amino acid
        ( C ) STRANDEDNESS:

(D) TOPOLOGY: linear (i i) MOLECULE TYPE: peptide (i x) FEATURE:
    (A) NAME/KEY: Region
    (B) LOCATION: 1..11
    (D) OTHER INFORMATION: /note= "At least one amino acid must have a D configuration."

(x i) SEQUENCE DESCRIPTION: SEQ ID NO:20:

```
Ala Lys Arg His His Gly Tyr Lys Arg Lys Phe
1               5                   10
```

(2) INFORMATION FOR SEQ ID NO:21:

(i) SEQUENCE CHARACTERISTICS:
        (A) LENGTH: 10 amino acids
        (B) TYPE: amino acid
        (C) STRANDEDNESS:
        (D) TOPOLOGY: linear (i i) MOLECULE TYPE: peptide (i x) FEATURE:
        (A) NAME/KEY: Region
        (B) LOCATION: 1..10
        (D) OTHER INFORMATION: /note= "At least one amino acid must have a D configuration."

(x i) SEQUENCE DESCRIPTION: SEQ ID NO:21:

```
Ala Lys Arg His His Gly Tyr Lys Arg Lys
1               5                   10
```

(2) INFORMATION FOR SEQ ID NO:22:

(i) SEQUENCE CHARACTERISTICS:
        (A) LENGTH: 9 amino acids
        (B) TYPE: amino acid
        (C) STRANDEDNESS:
        (D) TOPOLOGY: linear (i i) MOLECULE TYPE: peptide (i x) FEATURE:
        (A) NAME/KEY: Region
        (B) LOCATION: 1..9
        (D) OTHER INFORMATION: /note= "At least one amino acid must have a D configuration."

(x i) SEQUENCE DESCRIPTION: SEQ ID NO:22:

```
Ala Lys Arg His His Gly Tyr Lys Arg
1               5
```

(2) INFORMATION FOR SEQ ID NO:23:

(i) SEQUENCE CHARACTERISTICS:
        (A) LENGTH: 10 amino acids
        (B) TYPE: amino acid
        (C) STRANDEDNESS:
        (D) TOPOLOGY: linear (i i) MOLECULE TYPE: peptide (i x) FEATURE:
        (A) NAME/KEY: Region
        (B) LOCATION: 1..10
        (D) OTHER INFORMATION: /note= "At least one amino acid must have a D configuration."

(x i) SEQUENCE DESCRIPTION: SEQ ID NO:23:

```
Lys Arg His His Gly Tyr Lys Arg Lys Phe
1               5                   10
```

( 2 ) INFORMATION FOR SEQ ID NO:24:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Region
        ( B ) LOCATION: 1..12
        ( D ) OTHER INFORMATION: /note= "At least one amino acid
            must have a D configuration."

( x i ) SEQUENCE DESCRIPTION: SEQ ID NO:24:

Ala Lys Arg Phe His Gly Tyr Lys Arg Lys Phe His
1               5                   10

( 2 ) INFORMATION FOR SEQ ID NO:25:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Region
        ( B ) LOCATION: 1..12
        ( D ) OTHER INFORMATION: /note= "At least one amino acid
            must have a D configuration."

( x i ) SEQUENCE DESCRIPTION: SEQ ID NO:25:

Ala Lys Arg His Phe Gly Tyr Lys Arg Lys Phe His
1               5                   10

( 2 ) INFORMATION FOR SEQ ID NO:26:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Region
        ( B ) LOCATION: 1..12
        ( D ) OTHER INFORMATION: /note= "At least one amino acid
            must have a D configuration."

( x i ) SEQUENCE DESCRIPTION: SEQ ID NO:26:

Ala Lys Arg His His Gly Tyr Lys Arg Lys Phe Phe
1               5                   10

( 2 ) INFORMATION FOR SEQ ID NO:27:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Region -continued ( B ) LOCATION: 1..12
        ( D ) OTHER INFORMATION: /note= "At least one amino acid
            must have a D configuration."

( x i ) SEQUENCE DESCRIPTION: SEQ ID NO:27:

```
Ala   Lys   Arg   Phe   Phe   Gly   Tyr   Lys   Arg   Lys   Phe   His
1                       5                             10
```

( 2 ) INFORMATION FOR SEQ ID NO:28:

( i ) SEQUENCE CHARACTERISTICS:
    ( A ) LENGTH: 12 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( A ) NAME/KEY: Region
    ( B ) LOCATION: 1..12
    ( D ) OTHER INFORMATION: /note= "At least one amino acid
        must have a D configuration."

( x i ) SEQUENCE DESCRIPTION: SEQ ID NO:28:

```
Ala   Lys   Arg   Phe   Phe   Gly   Tyr   Lys   Arg   Lys   Phe   Phe
1                       5                             10
```

( 2 ) INFORMATION FOR SEQ ID NO:29:

( i ) SEQUENCE CHARACTERISTICS:
    ( A ) LENGTH: 12 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( A ) NAME/KEY: Region
    ( B ) LOCATION: 1..12
    ( D ) OTHER INFORMATION: /note= "At least one amino acid
        must have a D configuration."

( x i ) SEQUENCE DESCRIPTION: SEQ ID NO:29:

```
Ala   Lys   Arg   His   His   Lys   Tyr   Lys   Arg   Lys   Phe   His
1                       5                             10
```

( 2 ) INFORMATION FOR SEQ ID NO:30:

( i ) SEQUENCE CHARACTERISTICS:
    ( A ) LENGTH: 12 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( A ) NAME/KEY: Region
    ( B ) LOCATION: 1..12
    ( D ) OTHER INFORMATION: /note= "At least one amino acid
        must have a D configuration."

( x i ) SEQUENCE DESCRIPTION: SEQ ID NO:30:

```
Ala   Lys   Arg   His   His   Gly   Tyr   His   Arg   Lys   Phe   His
1                       5                             10
```

( 2 ) INFORMATION FOR SEQ ID NO:31:

( i ) SEQUENCE CHARACTERISTICS:
    ( A ) LENGTH: 12 amino acids (B) TYPE: amino acid
(C) STRANDEDNESS:
(D) TOPOLOGY: linear (ii) MOLECULE TYPE: peptide (ix) FEATURE:
(A) NAME/KEY: Region
(B) LOCATION: 1..12
(D) OTHER INFORMATION: /note= "At least one amino acid must have a D configuration."

(xi) SEQUENCE DESCRIPTION: SEQ ID NO:31:

```
Ala  Lys  Arg  His  His  Lys  Tyr  His  Arg  Lys  Phe  His
1                  5                        10
```

(2) INFORMATION FOR SEQ ID NO:32:

(i) SEQUENCE CHARACTERISTICS:
(A) LENGTH: 12 amino acids
(B) TYPE: amino acid
(C) STRANDEDNESS:
(D) TOPOLOGY: linear (ii) MOLECULE TYPE: peptide (ix) FEATURE:
(A) NAME/KEY: Region
(B) LOCATION: 1..12
(D) OTHER INFORMATION: /note= "At least one amino acid must have a D configuration."

(xi) SEQUENCE DESCRIPTION: SEQ ID NO:32:

```
Ala  Lys  Arg  His  His  Gly  Tyr  Phe  Arg  Lys  Phe  His
1                  5                        10
```

(2) INFORMATION FOR SEQ ID NO:33:

(i) SEQUENCE CHARACTERISTICS:
(A) LENGTH: 12 amino acids
(B) TYPE: amino acid
(C) STRANDEDNESS:
(D) TOPOLOGY: linear (ii) MOLECULE TYPE: peptide (ix) FEATURE:
(A) NAME/KEY: Region
(B) LOCATION: 1..12
(D) OTHER INFORMATION: /note= "At least one amino acid must have a D configuration."

(xi) SEQUENCE DESCRIPTION: SEQ ID NO:33:

```
Ala  Lys  Arg  Leu  Leu  Gly  Tyr  Lys  Arg  Lys  Phe  Leu
1                  5                        10
```

(2) INFORMATION FOR SEQ ID NO:34:

(i) SEQUENCE CHARACTERISTICS:
(A) LENGTH: 12 amino acids
(B) TYPE: amino acid
(C) STRANDEDNESS:
(D) TOPOLOGY: linear (ii) MOLECULE TYPE: peptide (ix) FEATURE:
(A) NAME/KEY: Region
(B) LOCATION: 1..12
(D) OTHER INFORMATION: /note= "At least one amino acid must have a D configuration."

(xi) SEQUENCE DESCRIPTION: SEQ ID NO:34:

```
Ala  Lys  Arg  Tyr  Tyr  Gly  Tyr  Lys  Arg  Lys  Phe  Tyr
1                  5                        10
```

(2) INFORMATION FOR SEQ ID NO:35:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Region
        (B) LOCATION: 1..12
        (D) OTHER INFORMATION: /note= "At least one amino acid must have a D configuration."

(xi) SEQUENCE DESCRIPTION: SEQ ID NO:35:

```
Ala  Gln  Arg  His  His  Gly  Tyr  Lys  Arg  Gln  Phe  His
1                  5                        10
```

(2) INFORMATION FOR SEQ ID NO:36:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Region
        (B) LOCATION: 1..12
        (D) OTHER INFORMATION: /note= "At least one amino acid must have a D configuration."

(xi) SEQUENCE DESCRIPTION: SEQ ID NO:36:

```
Ala  Lys  Gln  His  His  Gly  Tyr  Lys  Gln  Lys  Phe  His
1                  5                        10
```

(2) INFORMATION FOR SEQ ID NO:37:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Region
        (B) LOCATION: 1..12
        (D) OTHER INFORMATION: /note= "At least one amino acid must have a D configuration."

(xi) SEQUENCE DESCRIPTION: SEQ ID NO:37:

```
Ala  Gln  Gln  His  His  Gly  Tyr  Lys  Gln  Gln  Phe  His
1                  5                        10
```

ANTI-FUNGAL D-AMINO ACID HISTATIN-BASED PEPTIDES

RELATED APPLICATIONS

This Application is a Continuation-in-Part of and claims priority to U.S. Ser. No. 08/485,273, filed Jun. 7, 1995, and published as U.S. Pat. No. 5,631,228, which is a Continuation-in-Part of U.S. Ser. No. 08/287,717, filed Aug. 9, 1994, and published as U.S. Pat. No. 5,486,503 which is a File Wrapper Continuation of U.S. Ser. No. 08/145,030, filed Oct. 28, 1993 (now abandoned), which is a File Wrapper Continuation of U.S. Ser. No. 07/786,571, filed Nov. 1, 1991 (now abandoned), the contents of which are incorporated herein by reference in their entirety.

GOVERNMENT SUPPORT

The invention described herein was supported in whole or in part by Grant No. DE07652 from the National Institutes of Health, which have certain rights in the invention.

BACKGROUND OF THE INVENTION

The family of naturally occurring human histatins is a group of twelve low molecular weight, abundant in histidine, peptides found in human submandibular and parotid salivary secretions (Oppenheim et al. (1986), *J. Biol. Chem.* 261: 1177–1182; Oppenheim et al. (1988), *J. Biol. Chem.* 263: 7472–7477; Troxler et al. (1990), *J. Dent. Res.* 69: 2–6). The primary structure of the major family members (histatins 1, 3, and 5; 70–80% of the whole family) has shown that these proteins consist of 38, 32 and 24 amino acid residues, respectively. There is a high degree of homology among these three major histatins. Histatin 5 results from post-translational cleavage of histatin 3. Many of the smaller members of the histatin family may also, in fact, originate by post-translational proteolysis of histatins 1, 3 and 5 (Oppenheim et al. (1989), *Human Saliva: Clinical Chemistry and Microbiology Vol.* 1 CRC Press, Boca Raton, Fla., ed. Tenovuo, J. O.; Lal et al. (1992), *Arch. Oral Biol.* 37: 7–13). The genes that encode histatins 1 and 3 have been localized chromosomally (vanderSpek et al., (1989), *Am. J. Hum. Genet.* 45: 381–387) and sequenced (Sabatini, L. M. et al. (1989), *Biochem. Biophys. Res. Comm.* 160:495–502). Histatins 1 and 3 appear to be derived from separate genes.

The three major human histatins exhibit specific antimicrobial activities towards diverse oral microbiota. These histatins, at physiological concentrations, are capable of killing *Candida albicans* in both blastopore and mycelial forms (Pollock, J. J. et al. (1984), *Infect. Immun.* 44:702–707; Xu, T. et al. (1991), *Infect. Immun.* 59 (8): 2549–2554). Histatins are also capable of killing oral bacteria, including *Streptococcus mutans* (MacKay, B. J. et al. (1984), *Infect. Immun.* 44:695–701; Xu, T. et al. (1990), *J. Dent. Res.* 69: 239), *Porphyromonas gingivalis* (Colon et al. (1993), *J. Dent. Res.* 72: 322) and *Actinomyces viscosus* (Kalpidis et al. (1992) *J. Dent. Res.* 72: 305).

Infection with the yeast *Candida albicans* is a prevalent and, in some cases, life-threatening condition affecting otherwise healthy and immuno-compromised patients. Candidal vaginitis is estimated to affect 15 to 55% of healthy young women. Candidal infections often occur in diabetics, during pregnancy, and following medication with antibiotics, steroid hormones, or oral contraceptives. (Tapper-Jones, L. M. et al. (1981) *J. Clin. Pathol.* 34:706–11; Sobel, J. D. et al. (1984) *Infect. Immun.* 44:576–580). Oral candidiasis is an early opportunistic infection of Acquired Immune Deficiency Syndrome (AIDS) in individuals infected with human immunodeficiency virus type 1, as well as a complication of radiation and chemotherapy in cancer patients. (Yeh, C. -K. et al. (1988) *J. of Acquired Immune Deficiency Syndromes* 1:361–366). In addition, candidal infection of denture wearers plays a primary role in dental stomatitis, a prevalent oral problem among the elderly. (Pollock, J. J. et al. (1990) *NYS Dental J.* 56:36–38). Candidal infections of skin and urethra are widespread problems. In patients in intensive care and immuno-compromised patients, systemic fungal infection often leads to death, since there are few safe and effective anti-fungal pharmaceuticals for intravenous use. (Burnie, J. P. et al. (1985) *British Medical Journal* 290:746–748). Similarly, infections with various bacterial species can cause severe disease states and even death.

Although several anti-fungal agents (e.g., clotrimazole, miconazole, ketoconazole, and nystatin) and anti-bacterial agents (penicillin, streptomycin, tetracycline and chlorhexidine) are currently available, these agents are not completely effective, can lead to drug resistant organisms and can produce adverse side effects. Many are not appropriate for oral or systemic administration. Thus, a potent, naturally occurring anti-fungal or anti-bacterial substance would provide a significant improvement in the treatment of microbial infection.

SUMMARY OF THE INVENTION

This invention is based on substantially pure peptides which have anti-candidal or anti-bacterial activity equal to or greater than that of naturally occurring histatins but are smaller in size. These peptides have one or more D-amino acids in their amino acid sequences. These peptides represent defined portions of the amino acid sequences of naturally occurring human histidine-rich salivary proteins called histatins, which will be referred to herein as D-amino acid histatin-based peptides. The histatin-based peptides of this invention also include defined portions of the amino acid sequences of histatins with specific amino acid substitutions at specified positions of the sequences. As demonstrated herein, these D-amino acid histatin-based peptides have been shown to be superior in anti-candidal or anti-bacterial activity over the naturally occurring histatins. Thus, this invention provides compositions for treatment of fungal or bacterial infection comprising histatin-based peptides with defined amino acid sequences containing one or more D-amino acids. The D-amino acid peptides with significant anti-fungal or anti-bacterial activities have sequence portions of at least 8 amino acids and have the amino acid sequences of naturally occurring human histatins or histatin-based peptides derived from these histatins. A peptide with particularly significant anti-fungal or anti-bacterial activities is the peptide designated as peptide 113 (SEQ ID NO: 18). Homologs of peptide 113 with amino acid substitutions at particular positions in the peptide also have significant anti-fungal or anti-bacterial activity.

BRIEF DESCRIPTION OF FIGURES

FIGS. 1A–1D shows the amino acid sequences of human histatins 1 through 10 and the peptides 101, 102, 103, 104, 105, 113, 113-F4, 113-F5, 113-F12, 113-F4.5, 113-F4.5.12, 113-K6, 113-H8, 113-K6H8, 113-F8, 113-L4.5.12, 113-Y4.5.12, 113-Q2.10, 113-Q3.9, 113-Q2.3.9.10, 117, 118, 119, 120 and 129.

DETAILED DESCRIPTION OF THE INVENTION

Figure 2:
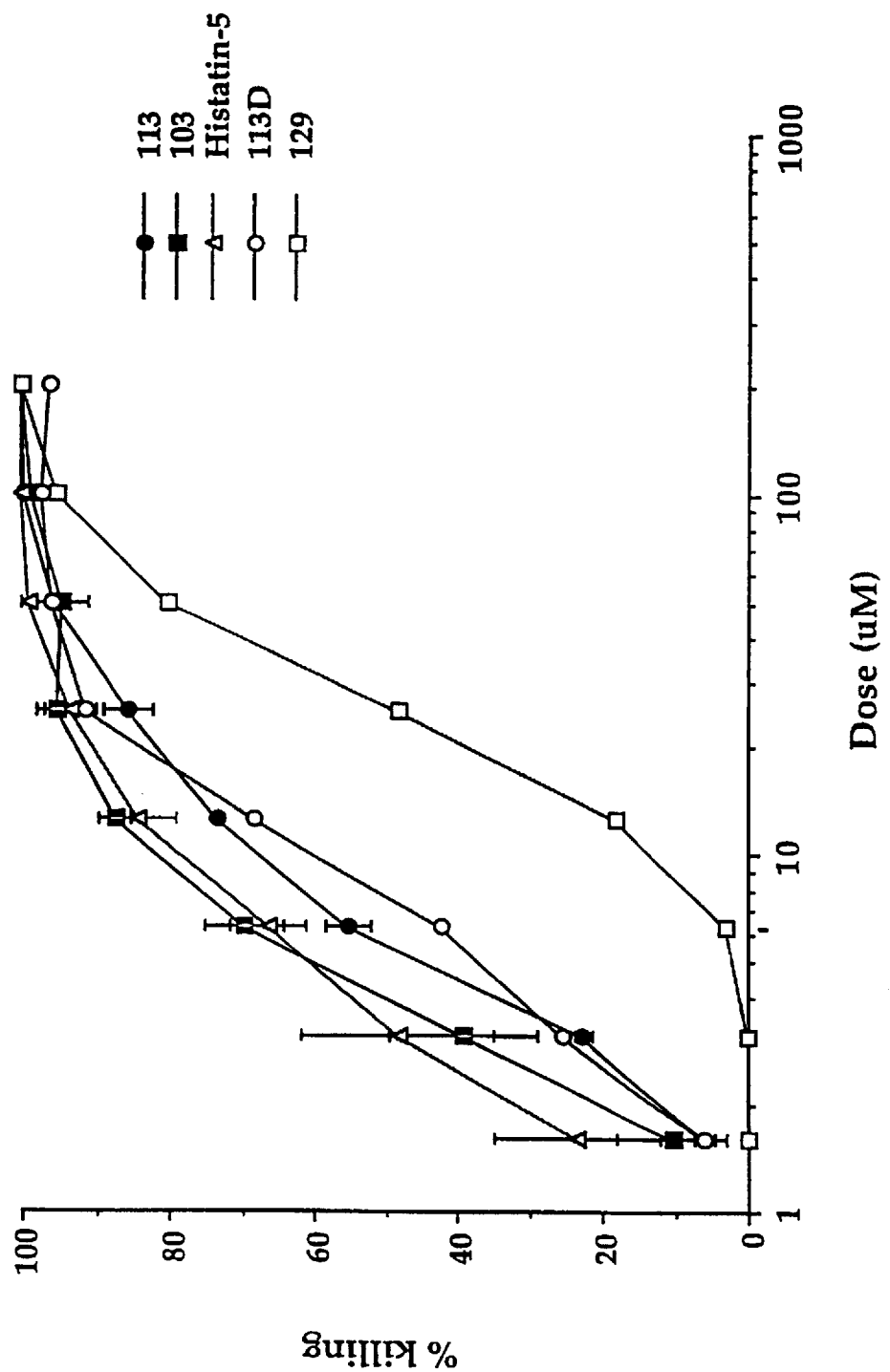
FIG. 2 is a graph that shows the % killing of *C. albicans* blastoconidia as a function of the concentration of histatin-5, peptide 103, peptide 113, peptide 113D and peptide 129.
Figure 3:
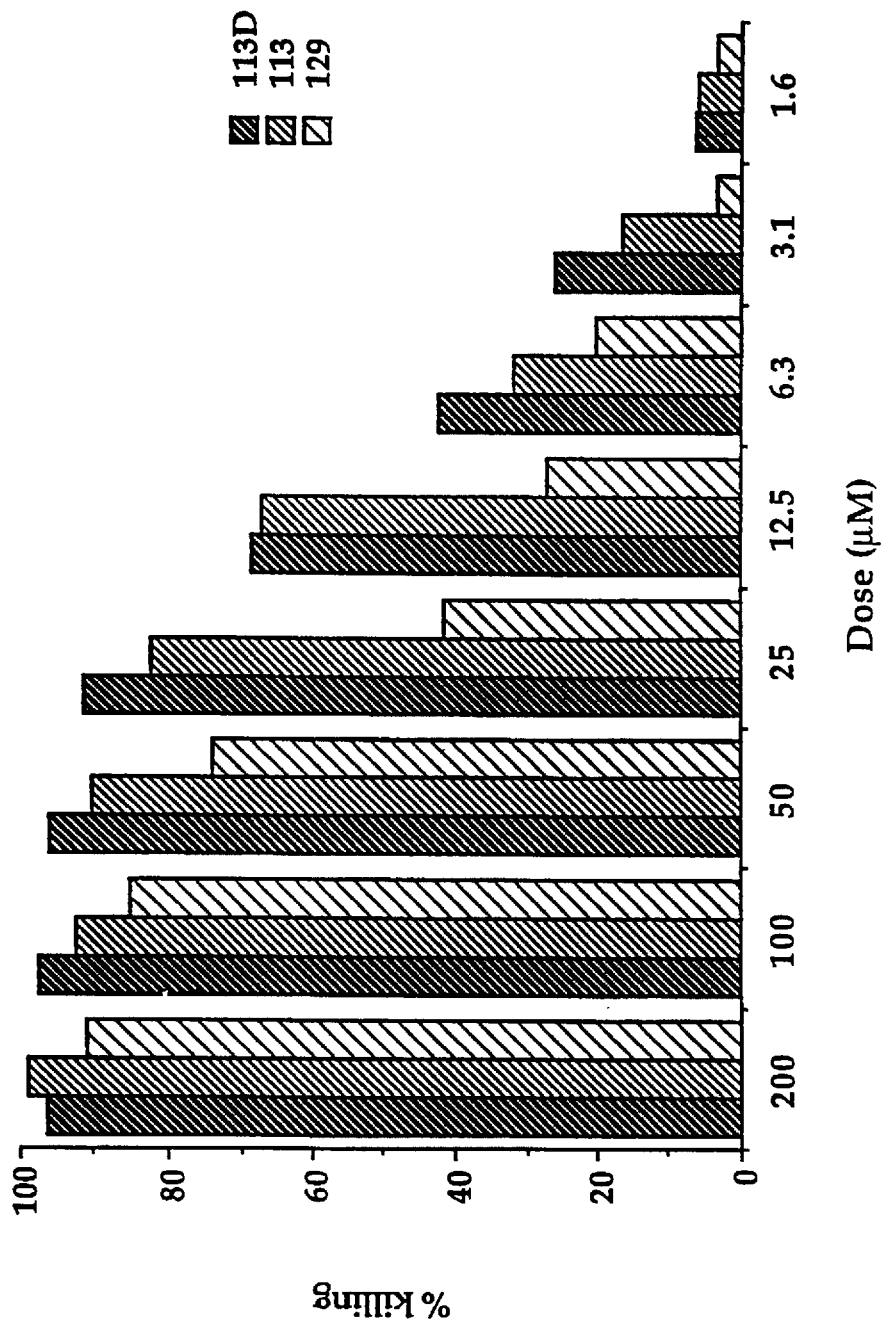
FIG. 3 is a bar graph that shows the % killing of *C. albicans* blastoconidia for different concentrations of peptide 113, peptide 113D and peptide 129.

This invention relates to peptides which have anti-fungal or anti-bacterial activity, in which the amino acid sequences represent defined portions of the amino acid sequences of naturally occurring human histidine-rich salivary proteins called histatins and where one or more of the amino acids of the amino acid sequences is of the D form. (Histatins are also referred to in the literature as histidine-rich proteins or HRPs.) Histatins are major salivary proteins which are synthesized in the parotid and submandibular-sublingual secretory glands of humans and Old World monkeys. (Azen, E. A. (1978) *Biochem. Genet.* 16:79–99). Histatins are believed to be part of an extraimmunologic defense system of the oral cavity. The anti-fungal activity of histatins, as well as their inhibitory effect on several oral bacteria (such as the cariogenic *Streptococcus mutans* and the periodontal pathogen *Porphyromonas gingivalis*), have been demonstrated in vitro. In addition, the observation that polyhistidine peptides inactivate herpes simplex virus in vitro and that whole saliva contains inhibitors of human immunodeficiency virus suggests the possibility that histatins may have anti-viral activity. These in vitro studies support potential clinical use of compositions containing histatins or histatin-based peptides that contain one or more D-amino acids for the treatment of local and systemic candidal infection, oral bacterial diseases, such as caries and periodontitis, systemic bacterial infection and viral infection. Vaginal, urethral, mucosal, respiratory, skin, ear, oral or ophthalmic fungal or bacterial infections are particularly susceptible to D-amino acid histatin-based peptide therapy. Microbes which are specifically amenable to D-amino histatin-based peptide therapy are:

a) *Candida albicans;*
b) *Actinomyces actinomycetemcomitans;*
c) *Actinomyces viscosus;*
d) *Bacteroides forsythus;*
e) *Bacteriodes fragilis;*
f) *Bacteriodes gracilis;*
g) *Bacteriodes ureolyticus;*
h) *Campylobacter concisus;*
i) *Campylobacter rectus;*
j) *Campylobacter showae;*
k) *Campylobacter sputorum;*
l) *Capnocytophaga gingivalis;*
m) *Capnocytophaga ochracea;*
n) *Capnocytophaga sputigena;*
o) *Clostridium histolyticum;*
p) *Eikenella corrodens;*
q) *Eubacterium nodatum;*
r) *Fusobacterium nucleatum;*
s) *Fusobacterium periodonticum;*
t) *Peptostreptococcus micros;*
u) *Porphyromonas endodontalis;*
v) *Porphyromonas gingivalis;*
w) *Prevotella intermedia;*
x) *Prevotella nigrescens;*
y) *Propionibacterium acnes;*
z) *Pseudomonas aeruginosa;*
aa) *Selenomonas noxia;*
bb) *Staphylococcus aureus;*
cc) *Streptococcus constellatus;*
dd) *Streptococcus gordonii;*
ee) *Streptococcus intermedius;*
ff) *Streptococcus mutans;*
gg) *Streptococcus oralis;*
hh) *Streptococcus pneumonia;*
ii) *Streptococcus sanguis;*
kk) *Treponema denticola;*
ll) *Treponema pectinovorum;*
mm) *Treponema socranskii;*
nn) *Veillonella parvula;* and
oo) *Wolinella succinogenes.*

The human histatin proteins have been isolated and sequenced. They have been shown to be a family of twelve related low molecular weight proteins. Comparison of the amino acid sequences of the histatins suggests that histatin 2 and histatins 4–12 may have originated from specific proteolytic cleavage of histatin 1 and histatin 3, respectively. (Oppenheim, F. G. et al. (1988), *J. Biol. Chem.* 263:7472–77; Troxler, R. F. et al. (1990), *J. Dent. Res.* 69(1):2–6). Cloning and sequence analysis of histatin cDNAs further suggest that the histatins are encoded by two homologous genetic loci, whose primary products are histatins 1 and 3. (Sabatini, L. M. et al. (1989), *Biochem. Biophys. Res. Comm.* 160:495–502; Vanderspek, J. C. et al. (1990), *Arch. Oral Biol.* 35(2):137–43).

The amino acid sequences of the anti-fungal and anti-bacterial peptides of this invention represent all or defined portions of the amino acid sequence of peptide 113 (SEQ ID NO: 18). In addition, the anti-fungal and anti-bacterial peptides of this invention include all or defined portions of peptide 113 (SEQ ID NO: 18) with amino acid substitutions at particular positions of the peptide.

Preferred embodiments of this invention are peptide 113 itself (SEQ ID NO: 18); fragments of peptide 113 containing at least an 8 amino acid sequence from this peptide; an amino acid sequence of at least 8 amino acids from peptide 113 where the glycine at position 6 is replaced by lysine, arginine or another basic amino acid; an amino acid sequence of at least 8 amino acids from peptide 113 where the lysine at position 8 is replaced by histidine, phenylalanine or another hydrophobic amino acid; an amino acid sequence of at least 8 amino acids from peptide 113 where one or more of the histidines at positions 4, 5 and 12 is (are) replaced by phenylalanine, tyrosine, leucine or another hydrophobic amino acid; an amino acid sequence of at least 8 amino acids from peptide 113 where one or both of the lysines at positions 2 and 10 is (are) replaced by glutamine, arginine or a combination of glutamine and arginine (when both lysines are replaced); and an amino acid sequence of at least 8 amino acids from peptide 113 where one or both of the arginines at positions 3 and 9 is (are) replaced by glutamine, lysine or a combination of glutamine and lysine (when both arginines are replaced). Combinations of these amino acid replacements in an amino acid sequence of at least 8 amino acids from peptide 113 are all preferred embodiments of the invention provided that a combination of 4 glutamines or any other group of 4 non-basic amino acids at positions 2, 3, 9 and 10 does not occur.

Specific preferred embodiments of this invention are histatin 1 (SEQ ID NO: 1), histatin 3 (SEQ ID NO: 3), histatin 5 (SEQ ID NO: 5), histatin 9 (SEQ ID NO: 9), peptide 101 (SEQ ID NO: 13), peptide 102 (SEQ ID NO: 14), peptide 103 (SEQ ID NO: 15), peptide 104 (SEQ ID NO: 16), peptide 105 (SEQ ID NO: 17), peptide 113 (SEQ ID NO: 18), histatin 11 (SEQ ID NO: 11), peptide 129 (SEQ ID NO: 23), peptide 117 (SEQ ID NO: 19), peptide 118 (SEQ ID NO: 20), peptide 119 (SEQ ID NO: 21), peptide 120 (SEQ ID NO: 22), peptide 113-F4 (SEQ ID NO: 24), peptide 113-F5 (SEQ ID NO: 25), peptide 113-F12 (SEQ ID NO: 26), peptide 113-F4.5 (SEQ ID NO: 27), peptide 113-F4.5.12 (SEQ ID NO: 28), peptide 113-K6 (SEQ ID NO: 29), peptide 113-H8 (SEQ ID NO: 30), peptide 113-K6H8 (SEQ ID NO: 31), peptide 113-F8 (SEQ ID NO: 32), peptide 113-L4.5.12 (SEQ ID NO: 33), peptide 113-Y4.5.12 (SEQ ID NO: 34), peptide 113-Q2.10 (SEQ ID NO: 35), and peptide 113-Q3.9 (SEQ ID NO: 36). The amino acid sequences of these preferred peptides are shown in FIGS. 1A–1D. Combinations of two or more of these D-amino acid peptides are also effective as anti-fungal or anti-bacterial compositions and are included as compositions of the invention. However, the combination of these peptides where glutamine occurs at positions 2, 3, 9 and 10, i.e. peptide 113-Q2.3.9.10 (SEQ ID NO: 37) is not a specifically preferred embodiment.

The D-amino acid peptides can be chemically synthesized. These D-amino acid peptides can be altered by minor chemical modifications, such as by adding small substituents or by modifying one or more of the covalent bonds within or between the amino acid residues, without significantly diminishing the anti-fungal or anti-bacterial activities of the peptides. Quite useful modifications are the addition of a substituent to either the amino terminus, the carboxyl terminus or to both ends of the peptide. These substituent addition modifications appear to stabilize the peptide in its active form and to aid in the prevention of enzymatic degradation of these peptides. These substituent groups are added to the amine, at the amino terminus, or to the carboxyl group, at the carboxyl terminus. The substituent groups can be somewhat bulky and may include one or more natural or modified amino acids. Particularly useful modifications are acetylation or carbamylation of the amino terminus of the peptide or amidation of the carboxyl terminus of the peptide. A combination of both modifications is especially useful. Such modifications appear to further increase the biological half-life of the peptides, beyond that afforded by incorporating D-amino acids in the sequence structure, before degradation, encapsulation, internalization or excretion occurs.

Figure 4:
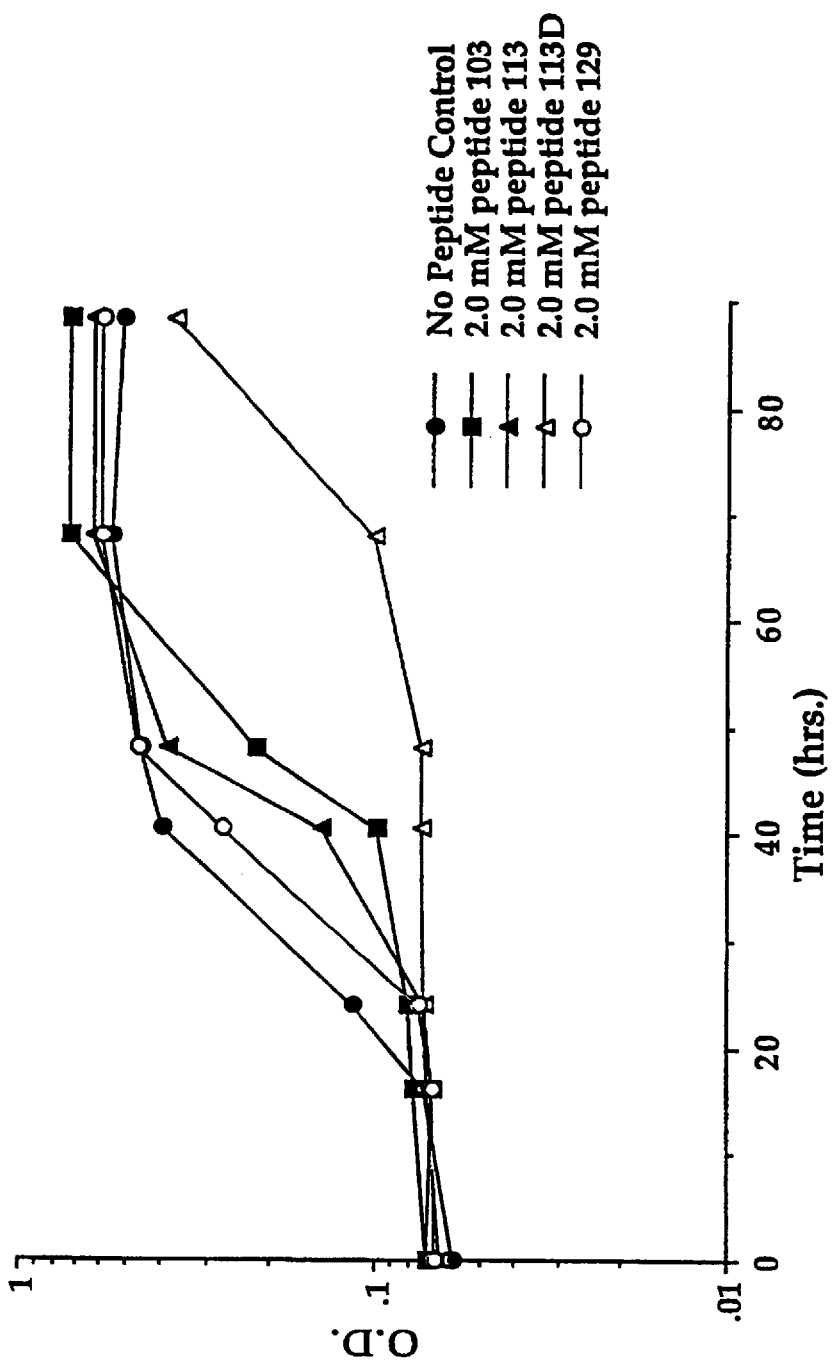
FIG. 4 is a graph that shows the amount of growth inhibition of *P. gingivalis* as a function of time for 2 mM concentrations of peptide 103, peptide 113, peptide 113D, and peptide 129, as well as when no histatin-based peptide is present.
Figure 5:
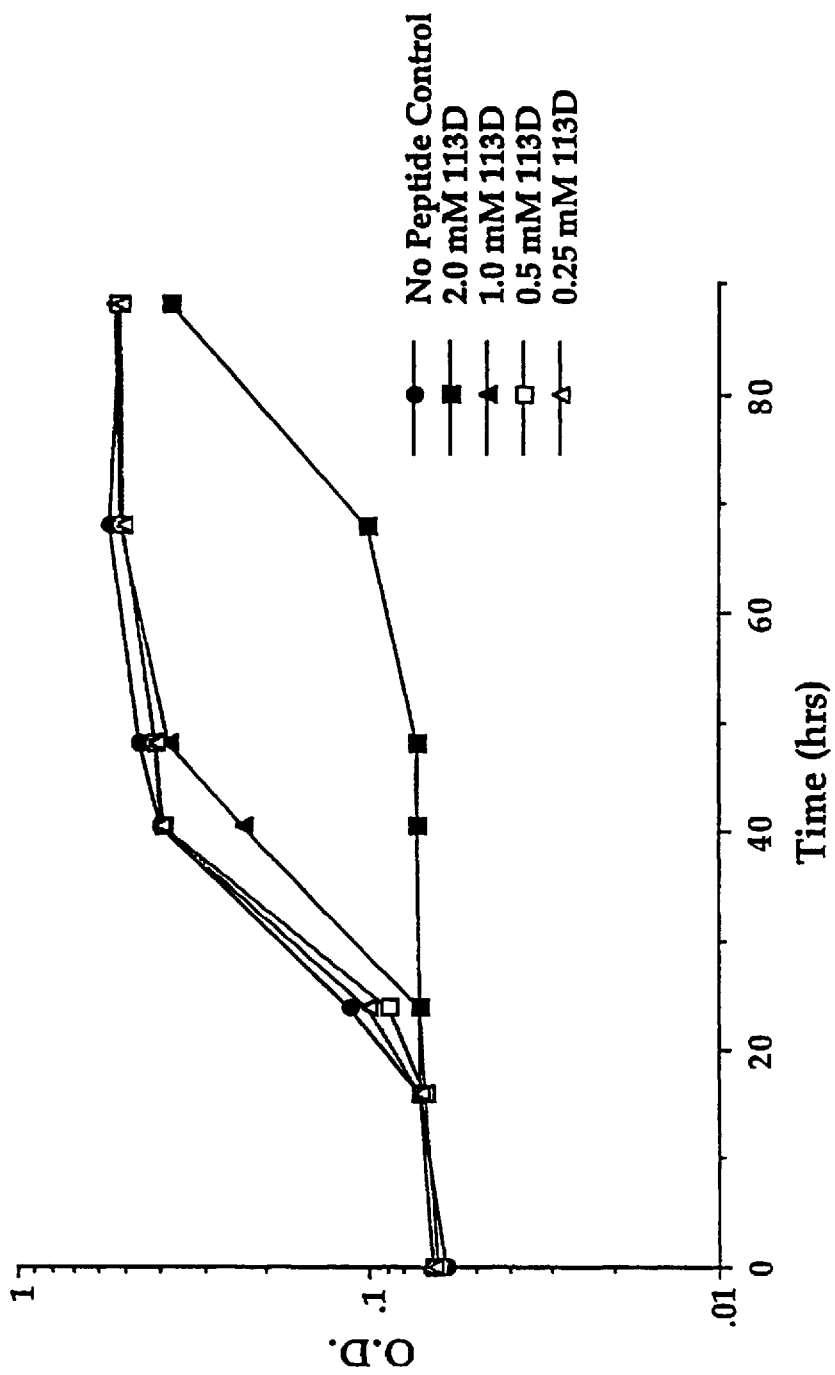
FIG. 5 is a graph that shows the amount of growth inhibition of *P. gingivalis* as a function of time for different concentrations of peptide 113D, as well as when no histatin-based peptide is present.
Figure 6:
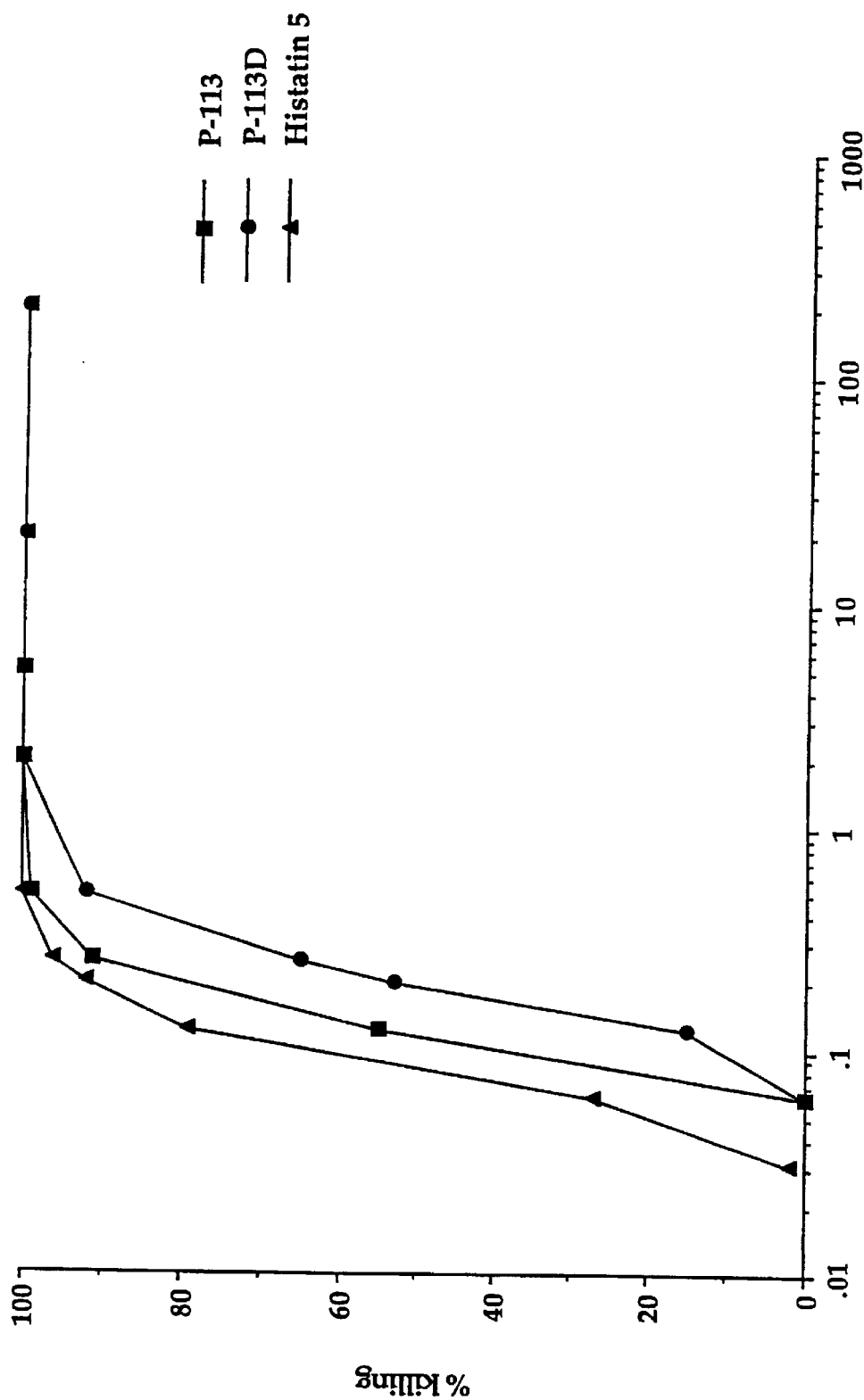
FIG. 6 is a graph that shows % killing of *P. aeruginosa* as a function of concentration of peptide 113, peptide 113D and histatin 5.
Figure 7:
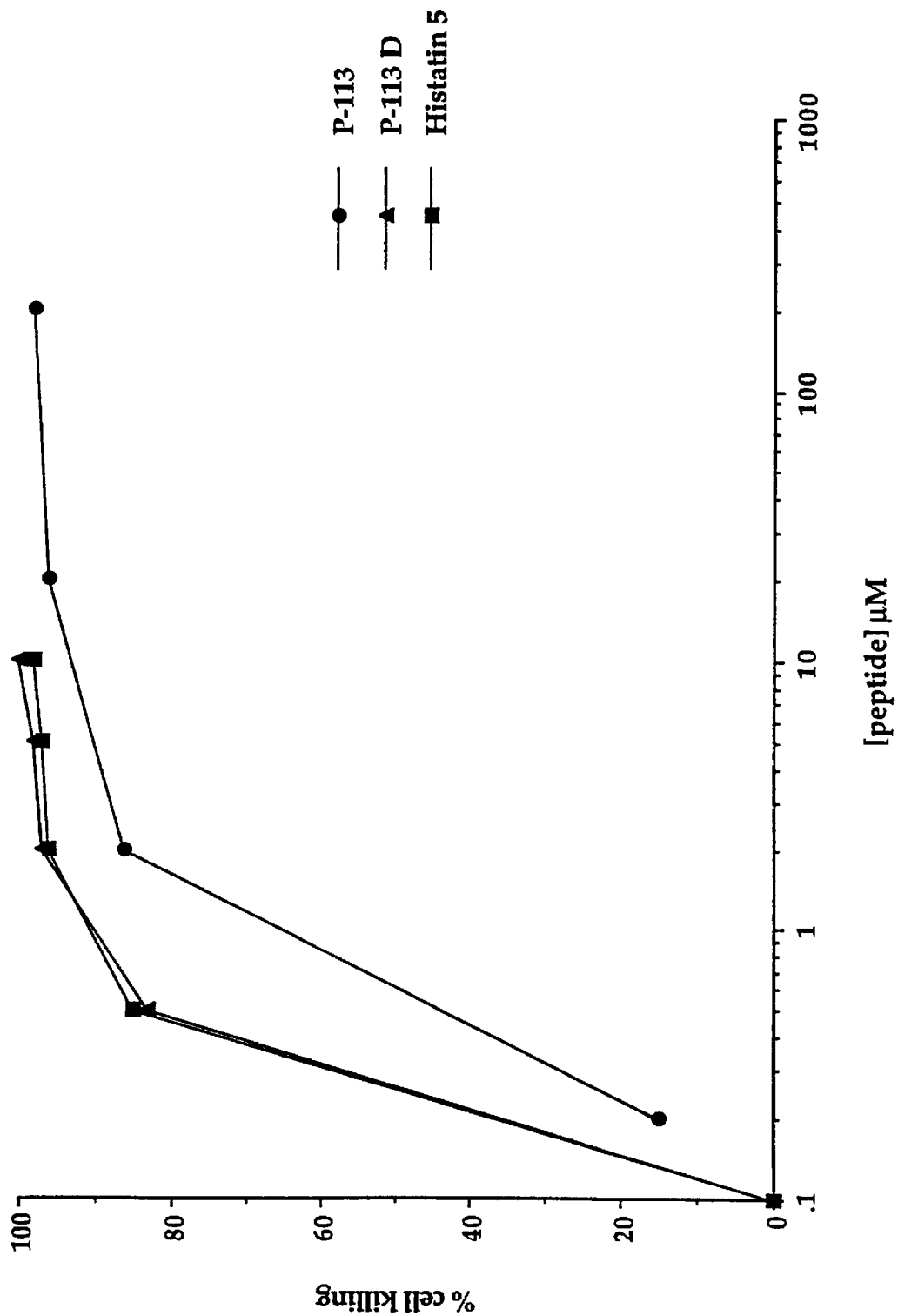
FIG. 7 is a graph that shows killing of *S. mutans* as a function of concentration of peptide 113, peptide 113D and histatin 5.

The peptides described herein were tested in assays designed to measure separately their effectiveness in killing of blastoconidia of C. albicans, in inhibiting the growth of P. gingivalis and in inhibiting clostripain activity. These assays are indicative of anti-fungal and anti-bacterial activities of the D-amino acid histatin-based peptides of the present invention. When tested in these assays, the D-amino acid histatin-based peptides of this invention were found surprisingly to have superior anti-candidal and anti-bacterial activity in comparison to the natural L-amino form of the histatin-based peptides (see FIG. 4) These anti-fungal and anti-bacterial activities are surprising in view of the size and truncated peptide form of some of these D-amino acid peptides.

The following is a description of the D-amino acid histatin-based peptides, the antifungal activities of the D-amino acid histatin-based peptides as measured in assays for killing of Candida blastoconidia, and the anti-bacterial activities of the histatin-based peptides as measured in assays for inhibition of P. gingivalis growth and inhibition of clostripain enzyme activity.

In the ensuing description, the D-amino acid histatins or histatin-based peptides will be designated by a D following the histatin or histatin-based peptide number, e.g. 113D.

D-Amino Acid Histatin-Based Peptides

The D-version of histatin-based peptide 113 (see FIGS. 1A–1D for the amino acid sequence) was prepared using standard solid-phase peptide synthesis techniques (see B. Merrifield, *Science* 232: 241–247 (1986)). In this instance, the carboxyl-terminal amino acid, histidine, which was attached to the solid support, was the L-enantiomer. The D-enantiomer was used for each of the remaining 11 residues, which were sequentially added to the L-histidine on the solid support to form the full length peptide. The resulting peptide was designated as 113D.

Solid supports can be obtained with D-amino acids covalently attached; thus, D-peptides can be prepared such that all residues, including the carboxyl-terminal residue, are the D-enantiomer.

This synthesis technique also allows the artisan to be selective in designating which amino acids are to be the D-enantiomer. In this manner, histatin-based peptides as well as histatins themselves can be synthesized with specific amino acids being of the D-enantiomeric form.

Anti-Fungal Activities of D-Amino Acid Histatin-Based Peptides

C. albicans is a dimorphic yeast. It can exist in a yeast or blastoconidial form, which upon germination develops into the hyphal or germinated form. While the germinated form is considered to be more invasive, most of the C. albicans isolates harvested from the oral cavities of healthy individuals appear to be in the blastoconidial form. (Arendorf, T. M. et al. (1980), *Arch. Oral Biol.* 25:1–10; Gow, N. A. R. et al. (1987), *Criti. Rev. Microbiol.* 15:73–78; Odds, F. C. (1988), *Candida and Candidosis*, 2nd ed., Bailliere Tindall, London, England). Anti-fungal activity of synthetic histatin 5, histatin-based peptide 113, synthetic peptide 113D and histatin-based peptide 129 was measured in assays designed to test the effectiveness of the peptides against the blastoconidia form of Candida. These assays, which measure killing of blastoconidia of *C. albicans*, are described in Xu et al., which is herein incorporated by reference. (Xu, T. et al. (1991), *Infect. Immun.* 59(8):2549–2554). Peptide 113D was found to be about equipotent with histatin 5, demonstrating its anti-fungal activity despite its size in comparison with histatin 5. Peptides 113 and 103 demonstrated fungicidal activity comparable to that of histatin 5 and D-amino acid histatin-based peptide 113D. Histatin-based peptide 129 has demonstrable fungicidal activity even though it is smaller than peptide 113. The anti-fungal potency of the histatin-based peptides appear to be a function of both the size and the amino acid sequence of the respective peptide. In particular, the anti-fungal potency of human histatins appears to reside in peptide 113 with selected subpeptides of peptide 113 maintaining at least partial anti-fungal activity. The D-amino acid version of peptide 113 retains the anti-fungal activity of peptide 113. Modifications of peptide 113 by making particular types of amino acid substitutions in this peptide result in peptides that retain anti-fungal activity. Additional modifications can be made by adding substituents to the amino terminus or to the carboxyl terminus.

Therapeutic Applications

The D-amino acid histatins and histatin-based peptides of this invention can be used in compositions and methods of treatment for fungal, and in particular, candidal infection, or for bacterial infection. These methods of treatment for fungal or bacterial infection apply to preventive treatment as well. The compositions may contain combinations of D-amino acid forms and non-D-amino acid forms of histatin-based peptides, in order to obtain maximum activity against all developmental forms of the fungus. The ionic strength, presence of various mono- and divalent ions, and pH of the compositions may be adjusted to obtain maximum anti-fungal or anti-bacterial activity of the histatin-based peptides, as described in Xu et al. (Xu, T. et al. (1991), *Infect. Immun.*59(8):2549–54). Carriers appropriate for administration of anti-fungal agents to the vagina, the urethra, the ear, the oral cavity, the respiratory system, the ophthalmic region, various mucosal regions and skin are known, and described, for instance, in U.S. Pat. No. 4,725,576 (*Fungicidal Polypeptide Compositions Containing L-His and Methods for Use Therefor* by J. J. Pollock and B. J. MacKay, Feb. 16, 1988). Compositions for treatment of systemic infection can be administered by various routes, such as intravenously or subdermally.

The compositions and methods for treatment of fungal or bacterial infections discussed above are not limited to use in humans, but can have veterinary applications as well.

Furthermore, the above-described compositions and methods for treatment of fungal infection can also be used for treatment of bacterial infections (e.g., of *S. mutans, P. aeruginosa* or *P. gingivalis*) and viral infections (e.g., of herpex simplex virus or human immunodeficiency virus type 1).

Clostripain Inhibition by D-Amino Acid Histatin-Based Peptides

Figure 8:
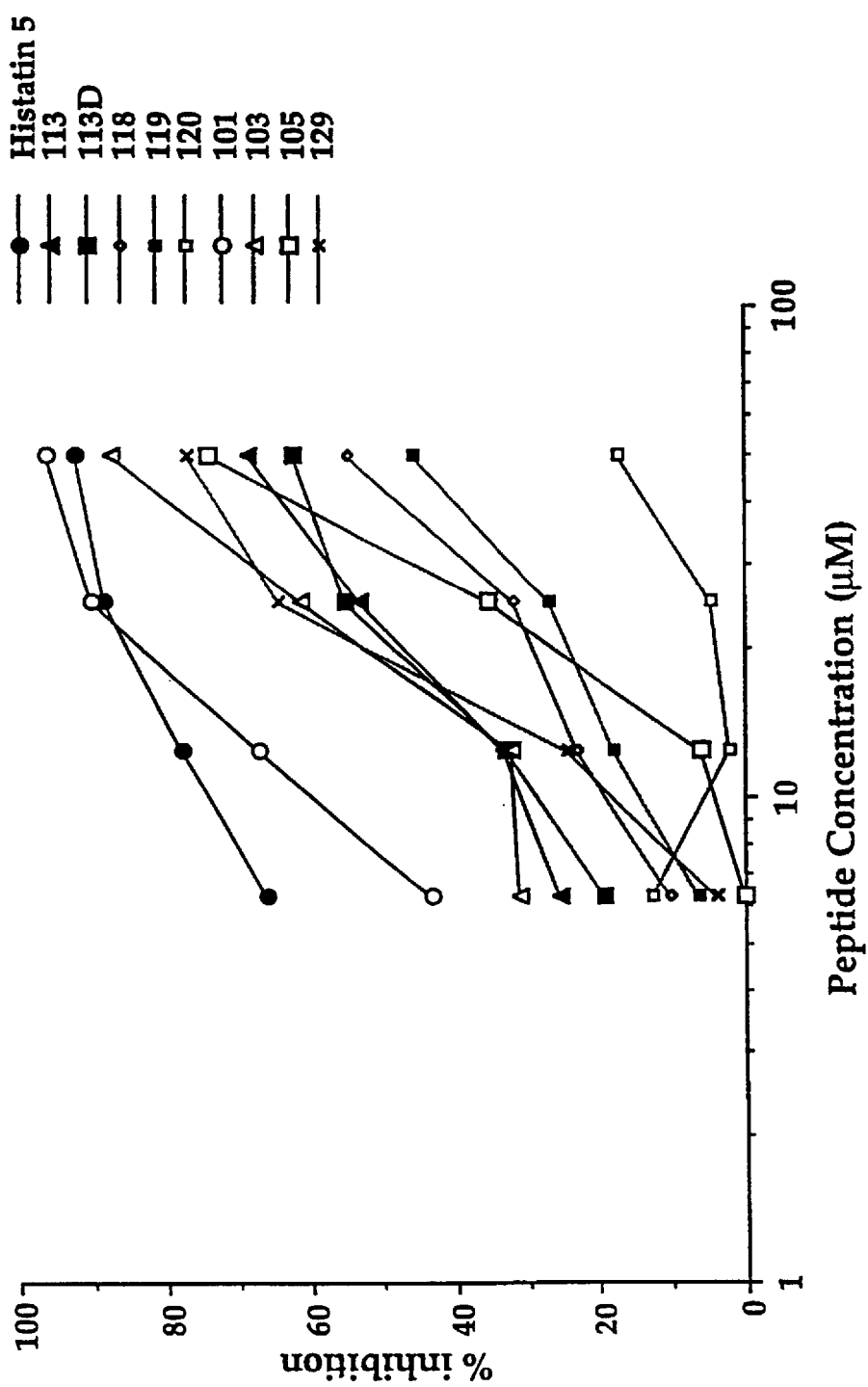
FIG. 8 is a graph that shows the % inhibition of clostripain activity as a function of the concentration of histatin 5, peptide 101, peptide 103, peptide 105, peptide 118, peptide 119, peptide 120, peptide 129, peptide 113 and peptide 113D.
Figure 9:
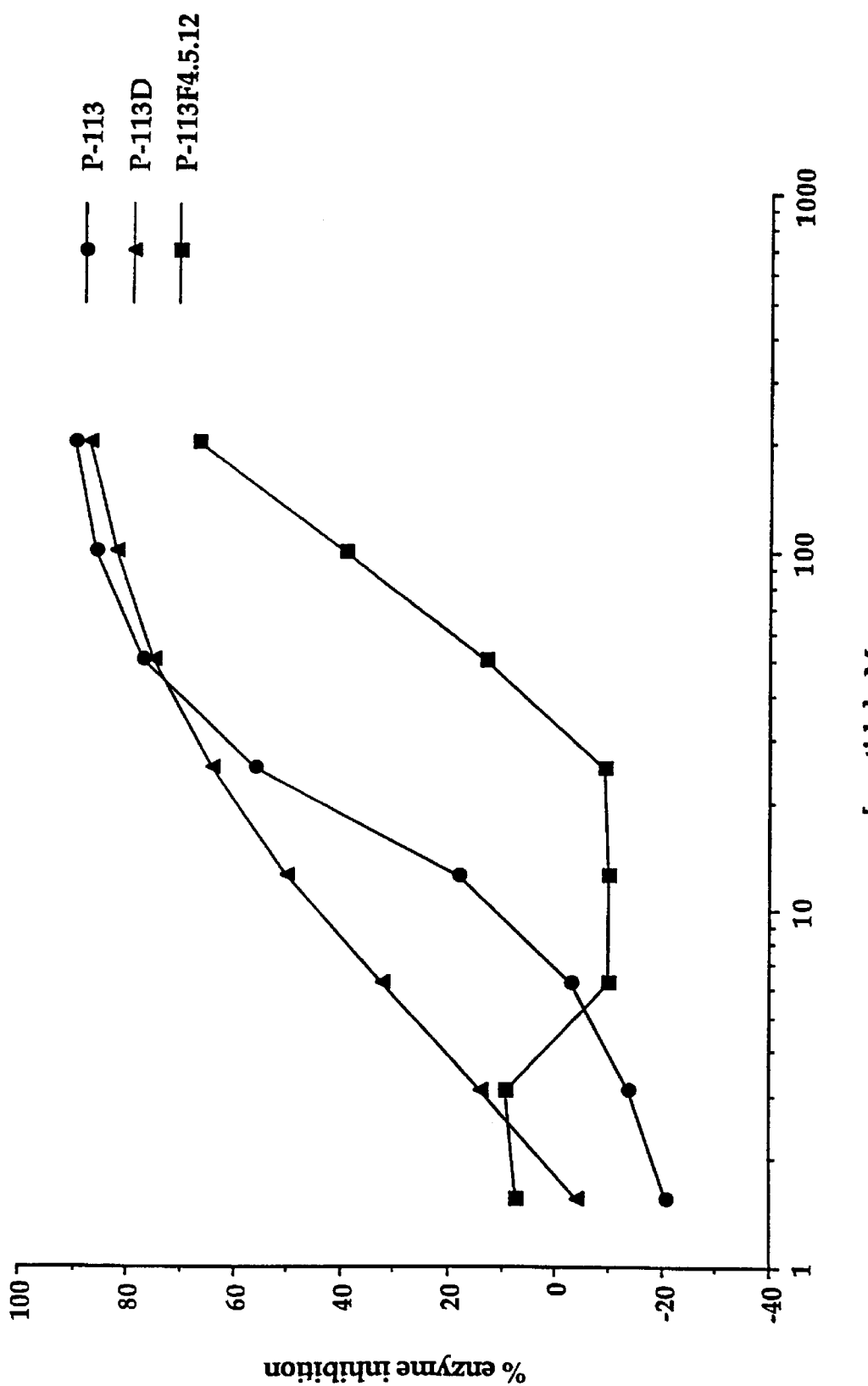
FIG. 9 is a graph that shows the k inhibition of clostripain activity as a function of the concentration of peptide 113D, peptide 113 and peptide 113-F4.5.12.

Clostripain is an endopeptidase enzyme synthesized by *Clostridium histolyticum*. This enzyme, with its protein degradative activity, can be inhibited by histatin 5 and by histatin-based peptides (see FIGS. 8 and 9). Thus, D-amino acid histatin-based peptides can inhibit bacterial function by inhibiting bacterial enzymes which are essential for the bacterial viability.

EXAMPLE 1

MATERIALS AND METHODS

A. Chemical Synthesis of Histatin-Based Peptides

Histatin-based peptides were synthesized by the solid phase method of Merrifield. (Merrifield, B. (1986) *Science* 232:341–47). Peptides were synthesized by a MilliGen/Bioresearch Sam-Two Peptide Synthesizer using Fmoc L-amino acid kits (Millipore, Bedford, Mass.) and purified on a TSK ODS-i20T $C_{18}$ column (5 μm, 4.6×250 mm) using RP-HPLC (Pharmacia-LKB). The purified peptides were quantified by amino acid analysis on a Beckman System 6300 amino acid analyzer.

B. *C. albicans* Killing (1) *C. albicans* Stock

A well-described strain of *C. albicans* was used in the bioassay. This strain, ATCC 44505, was originally isolated from the human oral cavity. Cultures were stored at 4° C. on Sabouraud dextrose agar plates (Difco Laboratories, Detroit, Mich.) until use. Stationary phase growth cells were obtained following growth at 30° C. for 18 h on Sabouraud. dextrose agar plates. Colonies were harvested and suspended in 10 mM potassium phosphate buffer (PPB), pH 7.4.

To initiate log phase growth, an aliquot of stock *C. albicans* was suspended in Sabouraud dextrose broth (Difco) and incubated at 30° C. in a shaking water bath. The growth phase was determined by taking aliquots of the culture at one hour intervals to monitor the optical density (O.D.) at 560 nm. Early log phase was obtained at 4 to 6 h, indicated by an O.D. of about 0.6. Log phase cells wereharvested and utilized in the blastoconidia killing assay in a manner identical to that described for stationary phase cells. A final concentration of $10^5$ cells/ml (either stationary or log phase fungus) was used in all assays.

(2) Suspension Buffers

The standard suspension buffer utilized in the blastospore killing assay was 0.01M PPB, pH 7.4. An alternate suspension buffer, N-2-hydroxyethylpiperazine-N'-2-ethanesulfonic acids (HEPES; Sigma Chemical Co., St. Louis, Mo.), pH 7.4, can also be utilized.

(3) Bioassays

The following assay was used to evaluate the effects of histatins on the killing of blastoconidia of *C. albicans*.

a. For the killing of blastoconidia assay, 50 μl aliquots of cells (2×$10^5$ cells/ml) diluted in suspension buffer were allowed to attach to a polystyrene 96-well micro-titer plate (COSTAR, Cambridge, Mass.) for 15 min at room temperature, and then incubated with an equal volume of a histatin or histatin peptide in suspension buffer for 1 h at 37° C. Controls were carried out in the absence of the histatin or histatin peptide. After incubation, wells were washed three times by centrifugation at 1000×g for 5 min and covered with aliquots of molten Sabouraud dextrose broth (Difco) containing 2% agarose (Sigma) at 45° C. The plate was then incubated at 30° C. for 8 h. Under such conditions, live cells will divide and begin to form colonies, while dead cells will remain as single cells. To determine the percentage of blastoconidia killed, a total of 100 single cells and/or colonies were counted under a Nikon inverted microscope at 400× magnification and the extent of killing was calculated using the formula: [1−(number of colonies in treated sample)/(number of colonies in control)]×100%.

(4) Statistical Analysis

Data were obtained by calculating the mean and standard deviation from triplicate assays. From the dose response relationship, doses effecting a 50% killing ($LD_{50}$).

C. BACTERIAL GROWTH INHIBITION AND CELL KILLING ASSAYS

(1) Bacterial Strains and Culture Conditions (a) The bacteria used in one investigation, *Porphyromonas gingivalis* strain A7A1-28, is a typical key pathogenic organism associated with destructive periodontal diseases. The bacteria were multiply subcultured in Enriched Todd Hewitt broth (ETHB, Difco Lab., Detroit, Mich.). Microorganisms were stored in the same broths containing 20% and 50% glycerol, at −20° C. and −70° C., respectively. These served as stock cultures from which all preparations originated.

Working stock cultures were maintained by weekly transfer to Brain Heart Infusion Anaerobic Sheep Blood Agar plates (BHIA, Becton Dickinson and Co., Cockeysville, Md.), and Trypticase Soy Anaerobic Sheep Blood Agar plates (TSA, Becton Dickinson and Co., Cockeysville, Md.). Plates were incubated for 3 to 4 days under strictly anaerobic conditions. For the bacteriostatic assay, bacteria were collected from plates, inoculated into the aforementioned broth and grown at 37° C., under strictly anaerobic conditions for 24 to 48 hours.

(b) Two other bacterial species were used in a bacterial cell killing assay system. These bacterial species were *Streptococcus mutans* strain SJ32 and *Pseudomonas aeruginosa* ATCC Accession Number 27853. The assays were performed using liquid overnight cultures (nutrient broth for *P. aeruginosa*; Todd Hewitt broth for *S. mutans*) from frozen stocks of these bacterial species. In the assay, the bacteria were diluted into assay buffer (10 mM Potassium Phosphate, pH 6.0 with 20 mM NaCl for *P. Aeruginosa*; and 10 mM Potassium Phosphate, pH 5.2 with 20 mM NaCl for *S.mutans*) to a concentration of $2\times10^5$ cfu/ml ($1\times10^9$ cfu/OD/ml) and combined with an equal volume (250 µl) of peptide to produce 500 µl incubation mixture with a final concentration of $10^5$ cfu/ml. Controls constituted buffer and bacteria but no peptide. After incubation at 37° C. (30 minutes incubation for *P. aeruginosa*; and 60 minutes incubation for *S. mutans*), the mixtures were plated onto agar media (nutrient agar for *P. aeruginosa*; and Todd Hewitt media with 0.5% glucose for *S. mutans*) and incubated at 37° C. until colonies developed. The mean number of colonies was determined and percent killing was determined from a minimum of 4 plates by comparing the colony number arising from control cultures versus the colony number arising from peptide-containing assay mixtures.

(2) Microdilution Bacteriostatic Assay

A modification of the typical microdilution assay (Rotilie et al., 1975) for the determination of minimal inhibitory concentration (MIC) of antimicrobial agents was utilized to investigate the bacteriostatic activity of the peptides. A standardized bacterial (*P. gingivalis*) inoculum was exposed to serially diluted antimicrobial peptides in an enriched broth medium that was suitable for the growth of anaerobic bacteria. The test was adapted for use in the 96-well microtiter plates. Results with the microdilution method have been shown to be comparable to the other known techniques for antimicrobial susceptibility such as the dilution method, the agar dilution method, and the broth-disk elution method (Rosenblatt et al., 1979). In the typical assay, the microtiter plate was observed at multiple time points after incubation for visible growth. The modification introduced here was based on the spectrophotometric reading of the microtiter plate after incubation.

Microorganisms from cultures maintained in the aforementioned plates were inoculated into 5 ml of the abovementioned broths and cultured overnight at 37° C. under strictly anaerobic conditions with continuous agitation on a minishaker (IKA-Labortechnik, Staufen i. Br., Germany). The bacteria were grown until reaching the late log phase and were then suspended in the same broths to an optical density (O.D.) of 0.1 at 560 nm. The peptides were diluted in 0.01M phosphate buffered saline (PBS), pH 7. Forty µl aliquots of peptide dilutions were added in each well of a U-bottom microtiter plate (Costar, Cambridge, Mass.) to give final concentrations of 2000, 1000, 500 and 250 µM. Twenty µl of bacterial inoculum was added to all the wells. Finally, 100 µl of the suitable broth were added to each well. The optical density of the wells of the microtiter plate was determined using a microplate reader set at 550 nm and the plate was then incubated under strictly anaerobic conditions for 24 hours. Controls were made by replacing the peptide dilutions with PBS alone. After the incubation, the is mixtures in each well were mixed manually to resuspend sedimented bacteria and the plate was read again. The experiments were conducted twice every time. The biologic activity was calculated according to the formula:

$$100-[[(\text{Fin ODexp-In ODexp})/(\text{Fin ODctr-In ODctr})]\times 100]$$

where:

Fin ODexp is the OD of the final experimental group;

In ODexp is the OD of the initial experimental group;

Fin ODctr is the OD of the final control group; and

In ODctr is the OD of the initial control group.

In addition, the % increase in time to reach mid-log phase growth was calculated.

The data presentation represent the means (±SEM) of at least 2 separate experiments.

D. CLOSTRIPAIN ASSAYS

Clostripain from *Clostridium histolyticum* (Sigma Chemical Corp., St. Louis, Mo.) was dissolved in deionized water to a concentration of 1 mg/mL (300 units/mg) and activated with the addition of 10 mmol/L DTT. To measure its hydrolytic activity, clostripain (6 units) was added to 50 nmol/L Hepes buffer, pH 7.5, containing 80 µmol/L BAPNA (benzoyl-arginine-p-nitroanilide), together with 5.6 µmol/L of histatin peptide inhibitor. As controls, assays were performed in the absence of any histatin peptide inhibitor. The activity was monitored continuously at 405 nm using a Molecular Devices $V_{Max}$ microtitre plate reader. The activities were determined from the maximum rates of substrate hydrolysis. Assays were done in duplicate, and the means normalized to the controls.

EXAMPLE 2

EFFECTS OF HISTATIN PEPTIDES, INCLUDING D-AMINO ACID HISTATIN-BASED PEPTIDES, ON FUNGAL OR BACTERIAL VIABILITY

FIGS. 2–9 summarize the results of the fungal killing, bacterial growth inhibition, bacterial cell killing and bacterial enzyme (clostripain) inhibition effects of D-amino acid histatin-based peptide 113D and several tested histatin peptides. For comparison purposes, the anti-fungal and anti-bacterial effects of peptide 113D and the non-D-amino acid histatin-based peptides were assessed with synthesized histatin 5 as a standard. Peptide 113D and histatin-based peptides 113, 118, 119, 120 and 129 have *C. albicans* blastoconidia killing, *P. gingivalis* growth inhibition, *P. aeruginosa* killing, *S. mutans* killing and clostripain inhibition effects. These antimicrobial effects are similar to those observed for histatin 5 and for histatin-based peptides 101–105. Although expected variations exist in anti-fungal and anti-bacterial effects between the tested peptides, the antimicrobial effects of the D-amino acid histatin-based peptides are comparable to those of histatin 5. These results demonstrate that D-amino acid histatin-based peptides are efficacious as anti-fungal or anti-bacterial agents. In particular, it should be noted that peptide 113D is efficacious for a longer period of time than its L-enantiomer congener (see FIG. 4). Thus, it is anticipated that the D-amino acid histatin-based peptides will have advantageous uses in comparison to L-enantiomeric histatin-based peptides. One of the reasons for this efficacy is that the D-amino acid form is less susceptible to biological degradation.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A composition for treating a fungal or bacterial infection comprising one or more peptides, wherein a peptide comprises one or more D-amino acids and has an amino acid sequence, of at least eight amino acids, selected from the group of amino acid sequences consisting of:

a) the amino acid sequence of peptide 113 as set forth in SEQ ID NO:18 where the glycine at position 6 is replaced by lysine, arginine or another basic amino acid;

b) the amino acid sequence of peptide 113 as set forth in SEQ ID NO:18 where the lysine at position 8 is replaced by histidine, phenylalanine or another hydrophobic amino acid;

c) the amino acid sequence of peptide 113 as set forth in SEQ ID NO:18 where at least on of the histidines at position 4, 5 and 12 is replaced by phenylalanine, tyrosine, leucine or another hydrophobic amino acid;

d) the amino acid sequence of peptide 113 as set forth in SEQ ID NO:18 where at least one of the lysines at positions 2 and 10 is replaced by glutamine, arginine or by another basic amino acid;

e) the amino acid sequence of peptide 113 as set forth in SEQ ID NO:18 where at least one of the arginines at positions 3 and 9 is replaced by glutamine, lysine, or by another basic amino acid; and f) any combination of peptides having the amino acid replacements of preceding sections a)–e) with the exception that glutamine or any other non-basic amino acid cannot simultaneously occupy positions 2, 3, 9 and 10 of the amino acid sequence.

2. A composition of claim 1 wherein the amino acid sequence of said peptide is selected from the group of amino acid sequences consisting of:

a) the amino acid sequence of peptide 113-F4 as set forth in SEQ ID NO:24;

b) the amino acid sequence of peptide 113-F5 as set forth in SEQ ID NO:25;

c) the amino acid sequence of peptide 113-F12 as set forth in SEQ ID NO:26;

d) the amino acid sequence of peptide 113-F4.5 as set forth in SEQ ID NO:27;

e) the amino acid sequence of peptide 113-F4.5.12 as set forth in SEQ ID NO:28;

f) the amino acid sequence of peptide 113-K6 as set forth in SEQ ID NO:29;

g) the amino acid sequence of peptide 113-H8 as set forth in SEQ ID NO:30;

h) the amino acid sequence of peptide 113-K6H8 as set forth in SEQ ID NO:31;

i) the amino acid sequence of peptide 113-F8 as set forth in SEQ ID NO:32;

j) the amino acid sequence of peptide 113-L4.5.12 as set forth in SEQ ID NO:33;

k) the amino acid sequence of peptide 113-Y4.5.12 as set forth in SEQ ID NO:34;

l) the amino acid sequence of peptide 113-Q2.10 as set forth in SEQ ID NO:35; and m) the amino acid sequence of peptide 113-Q3.9 as set forth in SEQ ID NO:36.

3. A composition of claim 1 wherein the peptide has a modification comprising the addition of at least one substituent to either the N-terminus, the C-terminus, or to both the N-terminus and C-terminus of said peptide.

4. A composition of claim 3 wherein at least one of said modifications of said peptide is selected from the group consisting of:

a) an acetyl or a carbamyl addition at the N-terminus; and b) an amide addition at the C-terminus.

5. A peptide comprising one or more D-amino acids and having an amino acid sequence, of at least eight amino acids, selected from the group of amino acid sequences consisting of:

a) the amino acid sequence of peptide 113 as set forth in SEQ ID NO:18 where the glycine at position 6 is replaced by lysine, arginine or another basic amino acid;

b) the amino acid sequence of peptide 113 as set forth in SEQ ID NO:18 where the lysine at position 8 is replaced by histidine, phenylalanine or another hydrophobic amino acid;

c) the amino acid sequence of peptide 113 as set forth in SEQ ID NO:18 where at least one of the histidines at position 4, 5 and 12 is replaced by phenylalanine, tyrosine, leucine or another hydrophobic amino acid;

d) the amino acid sequence of peptide 113 as set forth in SEQ ID NO:18 where at least one of the lysines at positions 2 and 10 is replaced by glutamine, arginine or by another basic amino acid;

e) the amino acid sequence of peptide 113 as set forth in SEQ ID NO:18 where at least one of the arginines at positions 3 and 9 is replaced by glutamine, lysine, or by another basic amino acid.

6. The peptide of claim 5 selected from the group of amino acid sequences consisting of:

a) the amino acid sequence of peptide 113-F4 as set forth in SEQ ID NO:24;

b) the amino acid sequence of peptide 113-F5 as set forth in SEQ ID NO:25;

c) the amino acid sequence of peptide 113-F 12 as set forth in SEQ ID NO:26;

d) the amino acid sequence of peptide 113-F4.5 as set forth in SEQ ID NO:27;

e) the amino acid sequence of peptide 113-F4.5.12 as set forth in SEQ ID NO:28;

f) the amino acid sequence of peptide 113-K6 as set forth in SEQ ID NO:29;

g) the amino acid sequence of peptide 113-H8 as set forth in SEQ ID NO:30;

h) the amino acid sequence of peptide 113-K6H8 as set forth in SEQ ID NO:31;

i) the amino acid sequence of peptide 113-F8 as set forth in SEQ ID NO:32;

j) the amino acid sequence of peptide 113-L4.5.12 as set forth in SEQ ID NO:33;

k) the amino acid sequence of peptide 113-Y4.5.12 as set forth in SEQ ID NO:34;

l) the amino acid sequence of peptide 113-Q2.10 as set forth in SEQ ID NO:35;

m) the amino acid sequence of peptide 113-Q3.9 as set forth in SEQ ID NO:36; and n) the amino acid sequence of peptide 113-Q2.3.9.10 as set forth in SEQ ID NO:37.

7. The peptide of claim 5 wherein the peptide has a modification comprising the addition of at least one substituent to either the N-terminus, the C-terminus, or to both the N-terminus and C-terminus of said peptide.

8. A peptide of claim 7 wherein at least one of said modifications of said peptide is selected from the group consisting of:

a) an acetyl or a carbamyl addition at the N-terminus; and b) an amide addition at the C-terminus.

9. A method for treating a fungal or bacterial infection in an individual comprising administering to said individual a therapeutically effective amount of one or more peptides, wherein a peptide comprises one or more D-amino acids and has an amino acid sequence, of at least eight amino acids, selected from the group of amino acid sequences consisting of:

a) the amino acid sequence of peptide 113 as set forth in SEQ ID NO:18 where the glycine at position 6 is replaced by lysine, arginine or another basic amino acid;

b) the amino acid sequence of peptide 113 as set forth in SEQ ID NO:18 where the lysine at position 8 is replaced by histidine, phenylalanine or another hydrophobic amino acid;

c) the amino acid sequence of peptide 113 as set forth in SEQ ID NO:18 where at least on of the histidines at position 4, 5 and 12 is replaced by phenylalanine, tyrosine, leucine or another hydrophobic amino acid;

d) the amino acid sequence of peptide 113 as set forth in SEQ ID NO:18 where at least one of the lysines at positions 2 and 10 is replaced by glutamine, arginine or by another basic amino acid;

e) the amino acid sequence of peptide 113 as set forth in SEQ ID NO:18 where at least one of the arginines at positions 3 and 9 is replaced by glutamine, lysine, or by another basic amino acid; and f) any combination of the peptides having amino acid replacements of preceding sections a)–e) with the exception that glutamine or any other non-basic amino acid cannot simultaneously occupy positions 2, 3, 9 and 10 of the amino acid sequence.

10. A method for treating a fungal or bacterial infection of claim 9 wherein the amino acid sequence of said one or more peptides is selected from the group of amino acid sequences consisting of:

a) the amino acid sequence of peptide 113-F4 as set forth in SEQ ID NO:24;

b) the amino acid sequence of peptide 113-F5 as set forth in SEQ ID NO:25;

c) the amino acid sequence of peptide 113-F12 as set forth in SEQ ID NO:26 ;

d) the amino acid sequence of peptide 113-F4.5 as set forth in SEQ ID NO:27;

e) the amino acid sequence of peptide 113-F4.5.12 as set forth in SEQ ID NO:28;

f) the amino acid sequence of peptide 113-K6 as set forth in SEQ ID NO:29;

g) the amino acid sequence of peptide 113-H8 as set forth in SEQ ID NO:30;

h) the amino acid sequence of peptide 113-K6H8 as set forth in SEQ ID NO:31;

i) the amino acid sequence of peptide 113-F8 as set forth in SEQ ID NO:32;

j) the amino acid sequence of peptide 113-L4.5.12 as set forth in SEQ ID NO:33;

k) the amino acid sequence of peptide 113-Y4.5.12 as set forth in SEQ ID NO:34;

l) the amino acid sequence of peptide 113-Q2.10 as set forth in SEQ ID NO:35; and m) the amino acid sequence of peptide 113-Q3.9 as set forth in SEQ ID NO:36.

11. A method for treating a fungal or bacterial infection of claim 9 wherein the peptide has a modification comprising the addition of at least one substituent to either the N-terminus, the C-terminus, or to both the N-terminus and C-terminus of said peptide.

12. A method for treating a fungal or bacterial infection of claim 11 wherein at least one of said modifications of said peptide is selected from the group consisting of:

a) an acetyl or a carbamyl addition at the N-terminus; and b) an amide addition at the C-terminus.

13. A method for treating a fungal or bacterial infection of claim 9 wherein said fungal or bacterial infection is selected from the group consisting of:

a) an infection of the oral cavity;

b) an infection of the vagina;

c) an infection of the urethra;

d) an infection of the ear;

e) an infection of the skin;

f) a respiratory infection;

g) a mucosal infection;

h) an ophthalmic infection; and i) a systemic infection.

14. A method for treating a fungal or bacterial infection of claim 13 wherein the fungus or bacterium is selected from the group consisting of:

a) *Candida albicans;* b) *Actinomyces actinomycetencomitans;* c) *Actinomyces viscosus;* d) *Bacteroides forsythus;* e) *Bacteriodes fragilis;* f) *Bacteriodes gracilis;* g) *Bacteriodes ureolyticus;* h) *Campylobacter concisus;* i) *Campylobacter rectus;* j) *Campylobacter showae;* k) *Campylobacter sputorum;* l) *Capnocytophaga gingivalis;* m) *Capnocytophaga ochracea;* n) *Capnocytophaga sputigena;* o) *Clostridium histolyticum;* p) *Eikenella corrodens;* q) *Eubacterium nodatum;* r) *Fusobacterium nucleatum;* s) *Fusobacterium periodonticum;* t) *Peptostreptococcus micros;* u) *Porphyromonas endodontalis;* v) *Porphyromonas gingivalis;* w) *Prevotella intermedia;* x) *Prevotella nigrescens;* y) *Propionibacterium acnes;* z) *Pseudomonas aeruginosa;* aa) *Selenomonas noxia;* bb) *Staphylococcus aureus;* cc) *Streptococcus constellatus;* dd) *Streptococcus gordonii;* ee) *Streptococcus intermedius;* ff) *Streptococcus mutans;* gg) *Streptococcus oralis;* hh) *Streptococcus pneumonia;* ii) *Streptococcus sanguis;* kk) *Treponema denticola;* ll) *Treponema pectinovorum;* mm) *Treponema socranskii;* nn) *Veillonella parvula;* and oo) *Wolinella succinogenes.*

15. A composition for treating a fungal or bacterial infection comprising one or more peptides, wherein a peptide comprises one or more D-amino acids and has a modification comprising the addition of at least one substituent to either the N-terminus, the C-terminus, or to both the N-terminus and C-terminus of said peptide, wherein said peptide has an amino acid sequence, of at least eight amino acids, selected from the group of amino acid sequences consisting of:
   a) the amino acid sequence of histatin 9 as set forth in SEQ ID NO:9;
   b) the amino acid sequence of histatin 11 as set forth in SEQ ID NO:11;
   c) the amino acid sequence of peptide 101 as set forth in SEQ ID NO:13;
   d) the amino acid sequence of peptide 102 as set forth in SEQ ID NO:14;
   e) the amino acid sequence of peptide 103 as set forth in SEQ ID NO:15;
   f) the amino acid sequence of peptide 104 as set forth in SEQ ID NO:16;
   g) the amino acid sequence of peptide 105 as set forth in SEQ ID NO:17;
   h) the amino acid sequence of peptide 113 as set forth in SEQ ID NO:18;
   i) the amino acid sequence of peptide 129 as set forth in SEQ ID NO:23;
   j) the amino acid sequence of peptide 117 as set forth in SEQ ID NO:19;
   k) the amino acid sequence of peptide 118 as set forth in SEQ ID NO:20;
   l) the amino acid sequence of peptide 119 as set forth in SEQ ID NO:21; and
   m) the amino acid sequence of peptide 120 as set forth in SEQ ID NO:22.

16. A composition of claim 15 wherein at least one of said modifications of said peptide is selected from the group consisting of:
   a) an acetyl or a carbamyl addition at the N-terminus; and
   b) an amide addition at the C-terminus.

17. A peptide comprising one or more D-amino acids and having a modification comprising the addition of at least one substituent to either the N-terminus, the C-terminus, or to both the N-terminus and C-terminus of said peptide, wherein said peptide has an amino acid sequence, of at least eight amino acids, selected from the group of amino acid sequences consisting of:
   a) the amino acid sequence of histatin 9 as set forth in SEQ ID NO:9;
   b) the amino acid sequence of histatin 11 as set forth in SEQ ID NO:11;
   c) the amino acid sequence of peptide 101 as set forth in SEQ ID NO:13;
   d) the amino acid sequence of peptide 102 as set forth in SEQ ID NO:14;
   e) the amino acid sequence of peptide 103 as set forth in SEQ ID NO:15;
   f) the amino acid sequence of peptide 104 as set forth in SEQ ID NO:16;
   g) the amino acid sequence of peptide 105 as set forth in SEQ ID NO:17;
   h) the amino acid sequence of peptide 113 as set forth in SEQ ID NO:18;
   i) the amino acid sequence of peptide 129 as set forth in SEQ ID NO:23;
   j) the amino acid sequence of peptide 117 as set forth in SEQ ID NO:19;
   k) the amino acid sequence of peptide 118 as set forth in SEQ ID NO:20;
   l) the amino acid sequence of peptide 119 as set forth in SEQ ID NO:21; and
   m) the amino acid sequence of peptide 120 as set forth in SEQ ID NO:22.

18. A composition of claim 17 wherein at least one of said modifications of said peptide is selected from the group consisting of:
   a) an acetyl or a carbamyl addition at the N-terminus; and
   b) an amide addition at the C-terminus.

19. A method for treating a fungal or bacterial infection in an individual comprising administering to said individual a therapeutically effective amount of one or more peptides wherein a peptide comprises one or more D-amino acids and has a modification comprising the addition of at least one substituent to either the N-terminus, the C-terminus, or to both the N-terminus and C-terminus of said peptide, wherein said peptide has an amino acid sequence, of at least eight amino acids, selected from the group of amino acid sequences consisting of:
   a) the amino acid sequence of histatin 9 as set forth in SEQ ID NO:9;
   b) the amino acid sequence of histatin 11 as set forth in SEQ ID NO:11;
   c) the amino acid sequence of peptide 101 as set forth in SEQ ID NO:13;
   d) the amino acid sequence of peptide 102 as set forth in SEQ ID NO:14;
   e) the amino acid sequence of peptide 103 as set forth in SEQ ID NO:15;
   f) the amino acid sequence of peptide 104 as set forth in SEQ ID NO:16;
   g) the amino acid sequence of peptide 105 as set forth in SEQ ID NO:17;
   h) the amino acid sequence of peptide 113 as set forth in SEQ ID NO:18;
   i) the amino acid sequence of peptide 129 as set forth in SEQ ID NO:23;
   j) the amino acid sequence of peptide 117 as set forth in SEQ ID NO:19;
   k) the amino acid sequence of peptide 118 as set forth in SEQ ID NO:20;
   l) the amino acid sequence of peptide 119 as set forth in SEQ ID NO:21; and
   m) the amino acid sequence of peptide 120 as set forth in SEQ ID NO:22.

20. A method for treating a fungal or bacterial infection of claim 19 wherein at least one of said modifications of said peptide is selected from the group consisting of:
   a) an acetyl or a carbamyl addition at the N-terminus; and
   b) an amide addition at the C-terminus.

21. A method for treating a fungal of bacterial infection of claim 19 wherein said fungal or bacterial infection is selected from the group consisting of:
   a) an infection of the oral cavity;
   b) an infection of the vagina;
   c) an infection of the urethra;
   d) an infection of the ear;
   e) an infection of the skin;
   f) a respiratory infection;
   g) a mucosal infection;
   h) an ophthalmic infection; and
   i) a systemic infection.

22. A method for treating a fungal or bacterial infection of claim 21 wherein the fungus or bacterium is selected from the group consisting of:
 a) *Candida albicans;*
 b) *Actinomyces actinomycetemcomitans;*
 c) *Actinomyces viscosus;*
 d) *Bacteroides forsythus;*
 e) *Bacteroides fragilis;*
 d) *Bacteroides graciclis;*
 f) *Bacteroides ureolyticus;*
 g) *Campylobacter concisus;*
 h) *Campylobacter rectus;*
 i) *Campylobacter showae;*
 j) *Campylobacter sputorum;*
 k) *Capnocytophaga gingivalis;*
 l) *Capnocytophaga ochracea;*
 m) *Capnocytophaga sputigena;*
 n) *Clostridium histolyticum;*
 o) *Eikenella corrodens;*
 p) *Eubacterium nodatum;*
 q) *Fusobacterium nucleatum;*
 s) *Fusobacterium periodonticum;*
 t) *Peptostreptococcus micros;*
 u) *Porphyromonas endodontalis;*
 v) *Porphyromonas gingivalis;*
 w) *Prevotella intermedia;*
 x) *Prevotella nigrescens;*
 y) *Propionobacterium acnes;*
 z) *Pseudomonas aeruginosa;*
 aa) *Selenomonas noxia;*
 bb) *Staphylococcus aureus;*
 cc) *Streptococcus constellatus;*
 dd) *Streptococcus gordonii;*
 ee) *Streptococcus intermedius;*
 ff) *Streptococcus mutans;*
 gg) *Streptococcus oralis;*
 hh) *Streptococcus pneumonia;*
 ii) *Streptococcus sanguis;*
 jj) *Treponoma denticola;*
 kk) *Treponoma pectinovorum;*
 ll) *Treponoma socranskii;*
 mm) *Veillonella parvula;* and
 nn) *Wolinella succinogenes.*

* * * * *